(12) United States Patent
Shin et al.

(10) Patent No.: US 9,089,564 B2
(45) Date of Patent: Jul. 28, 2015

(54) USE OF EC-SOD FOR TREATING ANGIOGENESIS-MEDIATED EYE DISEASES

(71) Applicant: The CATHOLIC UNIVERSITY OF KOREA INDUSTRY-ACADEMIC COOPERATION FOUNDATION, Seoul (KR)

(72) Inventors: Dong Heon Shin, Seoul (KR); Tae Yoon Kim, Seoul (KR)

(73) Assignee: The Catholic University of Korea Industry-Academic Cooperatior, Seoul (KR)

(*) Notice: Subject to any disclaimer, the term of this patent is extended or adjusted under 35 U.S.C. 154(b) by 0 days.

(21) Appl. No.: 14/325,107

(22) Filed: Jul. 7, 2014

(65) Prior Publication Data

US 2014/0335068 A1   Nov. 13, 2014

Related U.S. Application Data

(63) Continuation-in-part of application No. 12/532,539, filed as application No. PCT/KR2008/001636 on Mar. 24, 2008, now abandoned.

(30) Foreign Application Priority Data

Mar. 22, 2007 (KR) .................. 10-2007-0028327
Jun. 11, 2007 (KR) .................. 10-2007-0056973

(51) Int. Cl.
| A61K 38/00 | (2006.01) |
| C12N 9/02 | (2006.01) |
| A61K 38/44 | (2006.01) |

(52) U.S. Cl.
CPC ............ *A61K 38/446* (2013.01); *C12N 9/0089* (2013.01); *C12Y 115/01001* (2013.01)

(58) Field of Classification Search
CPC ................. C12N 9/0089; A61K 38/00; C12Y 101/01015
USPC ........................................................ 514/12.1
See application file for complete search history.

(56) References Cited

U.S. PATENT DOCUMENTS

| 6,011,067 A | 1/2000 | Hersh |
| 6,303,295 B1 * | 10/2001 | Taylor et al. ................. 435/6.16 |
| 7,740,839 B2 | 6/2010 | Kim et al. |
| 8,318,803 B2 | 11/2012 | Kim et al. |
| 2003/0228299 A1 * | 12/2003 | Droy-Lefaix et al. ....... 424/94.4 |

FOREIGN PATENT DOCUMENTS

| EP | 0307247 | 3/1989 |
| KR | 10-0676502 | 2/2007 |
| WO | 91/08291 | 6/1991 |

OTHER PUBLICATIONS

International Search Report issued on May 1, 2008 in the International Application No. PCT/KR2008/001636.
Written Opinion issued on May 1, 2008 in the International Application No. PCT/KR2008/001636.
Hua-Jun He, et al., "High-Level Expression of Human Extracellular Superoxide Dismutase in *Escherichia coli* and Insect Cells", Protein Expression and Purification 24, 2002, pp. 13-17, US.
Marikovsky, et al., "Cu/Zn Superoxide Dismutase Plays a Role in Angiogenesis", Int. J. Cancer, 2002, pp. 34-41, vol. 97, Wiley-Liss, Inc.
Marikovsky, et al., "Cu/Zn Superoxide Dismutase Plays Important Role in Immune Response", the Journal of Immunology, 2003, pp. 2993-3001, vol. 170, The American Association of Immunologists, Inc.
Notice of Allowance issued on Nov. 7, 2014, in U.S. Appl. No. 14/325,077.

* cited by examiner

*Primary Examiner* — Maryam Monshipouri
(74) *Attorney, Agent, or Firm* — H.C. Park & Associates, PLC

(57) ABSTRACT

A method for treating an angiogenesis-mediated eye disease, includes administering to a subject in need thereof an effective amount of EC-SOD protein, or a vector having a polynucleotide encoding the EC-SOD protein, to treat angiogenesis-mediated eye diseases.

1 Claim, 26 Drawing Sheets

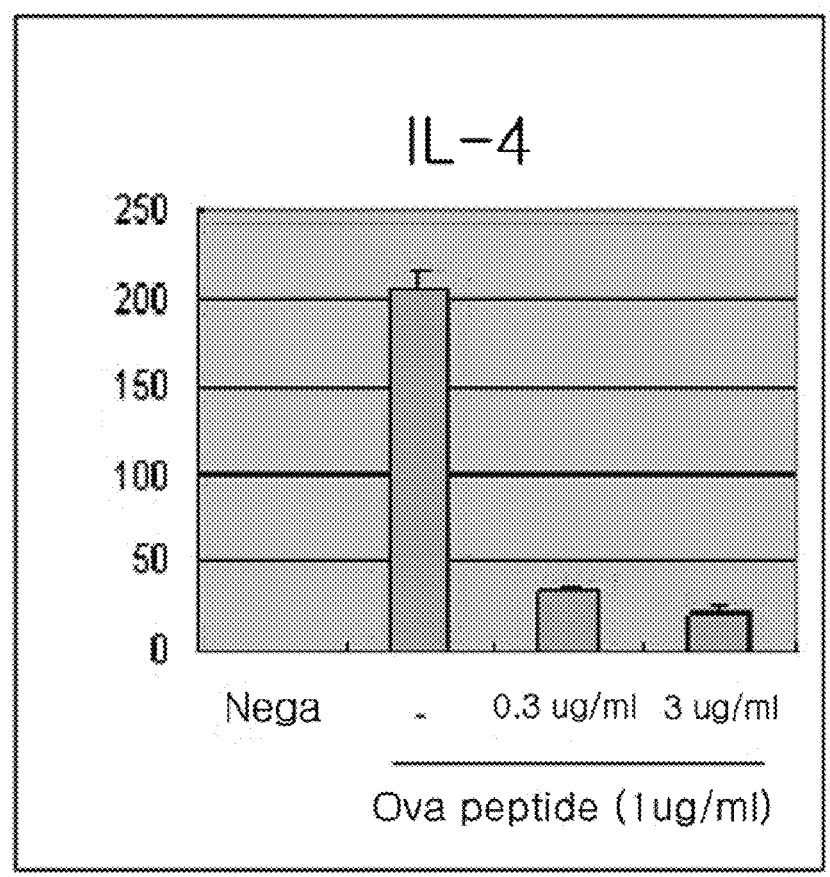

USE OF EC-SOD FOR TREATING ANGIOGENESIS-MEDIATED EYE DISEASES

CROSS-REFERENCE TO RELATED APPLICATIONS

This application is a continuation-in-part of U.S. patent application Ser. No. 12/532,539, filed on Sep. 22, 2009, which is the National Stage Entry of International Application No. PCT/KR2008/001636, filed on Mar. 24, 2008, and claims the benefit of and priority from Korean Patent Application No. 10-2007-0028327, filed on Mar. 22, 2007, and Korean Patent Application No. 10-2007-0056973, filed on Jun. 11, 2007, each of which is hereby incorporated by reference for all purpose as if fully set forth herein.

BACKGROUND

1. Field

The present disclosure relates to a novel use of an EC-SOD protein and a method for preparing the same. More particularly, the present disclosure relates to compositions for preventing or treating angiogenesis-mediated disease or allergic diseases which contain, an EC-SOD protein or a vector having a polynucleotide encoding the EC-SOD proteins an active ingredient.

2. Discussion of the Background

Superoxide dismutases (SODs) protect cells by removing reactive oxygen species and enabling other antioxidant enzymes, and SODs include Cu/Zn SOD (SOD 1) containing copper and zinc atoms, Mn SOD (SOD 2) containing a manganese atom, and extracellular superoxide dismutase (EC-SOD) present on the cell surface or in the extracellular fluid.

Particularly, EC-SOD contains copper and zinc atoms as in Cu/Zn SOD, but is characterized in that a heparin binding domain is present in the C-terminal end. Since EC-SOD has the heparin-binding domain, it is assumed that EC-SOD protect cell membranes by binding to the cell membranes. According to literature, EC-SOD plays a role in the body's defense mechanism in serums and extracellular matrices (Marklund et al, *Biochem. J.* 266, 213-219, 1990; Su et al., *Am J Respir Cell Mol Biol.*, February 16(2), 162-70, 1997; et al., *Thromb. Vasc. Bio.* 18, 157-167, 1998). In addition, it was reported that the heparin-binding domain of EC-'SOD acts as a nuclear localization signal, so that it is located within the nuclei of thymus and testis cells so as to protect genomic DNA from oxidative stress and to regulate the DNA transcription sensitive to oxidation-reduction reaction (Ookawara T et al., *BBRC*, 296, 54-61, 2002). The present inventors reported in Korean Patent Registration No. 10-0676502 that EC-SOD has the effect of treating skin diseases such as psoriasis by removing reactive oxygen species in skin cells and inhibiting the over-proliferation of epidermal cells.

Angiogenesis is the process by which new capillary blood vessels are formed from preexisting vessels. Angiogenesis normally occurs only in some specific situations, including embryonic development, wound healing and the female reproductive cycle, and does not substantially occur in normal conditions. However, when angiogenesis is not regulated correctly, diseases such as cancer may be induced.

The angiogenic process includes stimulation of endothelial cell growth by tumor cytokine, vascular endothelial growth factor (VEGF) and basic fibroblast growth factor (bFGF), degradation of extracellular matrix proteins by matrix metalloprotease (MMP), and migration of endothelial cells, which is mediated by membrane adhesion molecules, endothelial cell differentiation and tube formation (Bussolino, F. et al., *Trends Biochem. Sci.* 22:251-256, 1997; Kuwano, M. et al., *Intern. Med.* 40:565-572, 2001; Risau, W. Angiogenesis and endothelial cell function. *Arzneimittelforschung* 44:416-417, 1994). Thus, inhibition of these above processes has been proposed as a new therapeutic strategy for the treatment of angiogenesis-mediated diseases, including cancer and other human diseases. For this purpose, a variety of angiogenesis inhibitors have been developed. The inhibitors, which are natural or synthetic, include protease inhibitors, tyrosine kinase inhibitors, chemokines, interleukins, and proteolytic fragments of matrix proteins (Abedi, H. et. al., *J. Biol. Chem.* 272:15442-15451, 1997; Cao, Y., *Int. J. Biochem. Cell Biol.* 33:357-369, 2001; Fong, T. A et al., *Cancer Res.* 59:99-106, 1999; Kwon, H. J. et al., Acalycigorgia inermis. *J. Microbiol. Biotechnol.* 11:656-662, 2001). These antiangiogenic molecules affect various processes, including the inhibition of endothelial cell proliferation, migration, protease activity, and tubule formation, as well as the induction of apoptosis (Folkman, J. et. al., *Semin. Cancer Biol.* 3:89-96, 1992; Kishi, K. et al., *Nippon Rinsho* 58:1747-1762, 2000; Marme, D., *Onkologie* 1:1-5, 2001). The antiangiogenic function of many of these molecules has been well studied in vitro and in vivo, and some antiangiogenic drugs are currently being tested in clinical trials (Deplanque, G. et. al., *Eur. J. Cancer* 36:1713-1724, 2000; Liekens, et. al., *Biochem. Pharmacol.* 61:253-270, 2001; Mross, K., *Drug Resist. Updat.* 3: 223-235, 2000).

Reactive oxygen species have been reported to be major regulators of angiogenesis (Jolanta Grzenkowicz-Wydra, et. al., *Mol Cell Biochem.*, 264(1-2):169-81, 2004), but the relationship between SODs, which remove reactive oxygen species, and angiogenesis, has not yet been sufficiently examined. It was recently reported that the overexpression of Cu/Zn SOD (SOD 1), having copper and zinc atoms, among SODs, leads to the stimulation of angiogenesis, and thus the inhibition of SOD1 leads to the inhibition of angiogenesis (Jolanta Grzenkowicz-Wydra, et. al., *Mol Cell Biochem.*, 264 (1-2):169-81, 2004). In addition, it was reported that ATN-224, which is an inhibitor of SOD1, inhibits angiogenesis, and thus can be used as an anticancer agent, and it is in a phase II trial (Juarez et al. *Clin Cancer Res.*, 12: 4974-4982, 2006). However, there is no report on the relationship between EC-SOD and angiogenesis.

With the development of industry, allergy-causing factors have increased due to environmental pollution, an increase in new synthetic substances and a change in residential environments, and thus the number of people suffering from asthma and allergies has gradually increased. The function of the body to show specific resistance against foreign matter, which has invaded the body, is referred to as immunity. An allergy is a hypersensitive immune reaction, and typical allergic diseases include atopic dermatitis, bronchial asthma and pollenosis. Clinical symptoms resulting from allergic reactions are broadly classified into specific immune reactions at an early stage, and inflammatory reactions at a late stage. These immune reactions are mostly mediated by mast cells, which are widely distributed in the systemic organs, including the skin, the respiratory organ, the gastrointestinal mucosa, the brain, around lymphatic vessels and around blood vessels and to cause allergic reactions. Mediators that activate mast cells include an IgE antibody (FcεRI) bound to a high-affinity immunoglobulin E (IgE) receptor (FcεRI) located on the cellular membrane, compound 48/80 and the like. The activation mechanism of mast cells by IgE antibody is as follows.

When an IgE antibody bound to an IgE receptor forms a bridge with an antigen, substances, such as histamine, chondroitin sulfate, heparin and protease, stored in the mast cell granules, are released through the action of phospholipase C, protein phosphatase C and calcium ions, thus mediating the early reaction stage. Among the chemical substances, including histamine, cause clinical symptoms occurring in the early allergic reaction, histamine accounts for the largest amount. In other words, in the early allergic reaction, the expression of histamine is predominant, and clinical symptoms resulting therefrom include vasodilation, edema and the like.

Currently, antihistamine drugs or steroidal drugs are frequently used to treat allergies. However, these drugs mostly have temporary effects, and in many cases, cause serious side effects. Accordingly, there is an urgent need to develop a novel substance, which has the effect of preventing and treating rapidly increasing allergic diseases, and at the same time, has reduced side effects and lasting effects. However, whether EC-SOD has the effect of treating allergic diseases is not yet known.

Also, even if the EC-SOD has various activities, when a method for producing the EC-SOD in large amounts is not developed, there is a problem in that the EC-SOD cannot be efficiently used in industry. However, mass-production methods for proteins, developed to date, comprise transforming host cells, such as E. coli cells, with expression vectors, and inducing the expression of proteins in the transformed cells, and the mass production of proteins has problems in that it often causes the formation of inclusion bodies, and thus the original activities of the proteins are eliminated or reduced.

The present inventors have conducted studies on the EC-SOD protein, and as a result, have found that the EC-SOD shows an activity of inhibiting diseases caused by angiogenesis or allergic diseases. On the basis of this finding, the present inventors have developed a method for preparing the EC-SOD protein having the activity.

SUMMARY

The present disclosure provides a composition for preventing or treating angiogenesis-mediated diseases comprising an EC-SOD protein, as an active ingredient.

In another aspect, the present disclosure provides a composition for preventing or treating angiogenesis-mediated diseases comprising a vector having a polynucleotide encoding an EC-SOD protein, as an active ingredient.

In still another aspect, the present disclosure provides a composition for preventing or treating allergic diseases comprising an EC-SOD protein, as an active ingredient.

In still another aspect, the present disclosure provides a composition for preventing or treating allergic diseases comprising a vector having a polynucleotide encoding an EC-SOD protein, as an active ingredient.

In still another aspect, the present disclosure provides a method of preparing an EC-SOD protein.

The present disclosure provides a composition for preventing or treating angiogenesis-mediated diseases comprising an EC-SOD protein, as an active ingredient.

In another aspect, the present disclosure provides a composition for preventing or treating angiogenesis-mediated diseases comprising a vector having a polynucleotide encoding an EC-SOD protein, as an active ingredient.

In still another aspect, the present disclosure provides a composition for preventing or treating allergic diseases comprising an EC-SOD protein, as an active ingredient.

In still another aspect, the present disclosure provides a composition for preventing or treating allergic diseases comprising a vector having a polynucleotide encoding an EC-SOD protein, as an active ingredient.

In yet another aspect, the present disclosure provides a method for preparing an EC-SOD protein, the method comprising: (a) cloning into an expression vector a polynucleotide encoding the EC-SOD protein; (b) introducing the expression vector into host cells to transform the host cells; (c) culturing the transformed host cells to express the EC-SOD protein in the cells; (d) collecting the inclusion body of the expressed EC-SOD; and (e) dissolving the inclusion body and inducing the refolding of the inclusion body.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the principles of the invention.

FIG. 6A: wild type mouse, FIG. 6B: EC-SOD overexpressed mouse, FIG. 6C: UV irradiated wild type mouse, and FIG. 6D: UV irradiated EC-SOD overexpressed mouse.

FIG. 8A: wild type mouse, FIG. 8B: EC-SOD overexpressed mouse, FIG. 8C: UV irradiated wild type mouse, and FIG. 8D: UV irradiated EC-SOD overexpressed mouse.

FIG. 10A: control, FIG. 10B: UVB irradiated, FIG. 10C: recombinant EC-SOD treatment+UVB irradiation, and FIG. 10D: recombinant EC-SOD treatment.

FIGS. 13A and 13B are results confirming by identifying the secretion level of IL-4 (FIG. 13 A) and IFN-γ (FIG. 13B) whether treatment of recombinant EC-SOD protein has the effect on T-cell differentiation (neg.: negative control –: treated with antigen (Ova peptide) only).

DETAILED DESCRIPTION OF THE ILLUSTRATED EMBODIMENTS

Figure 1:
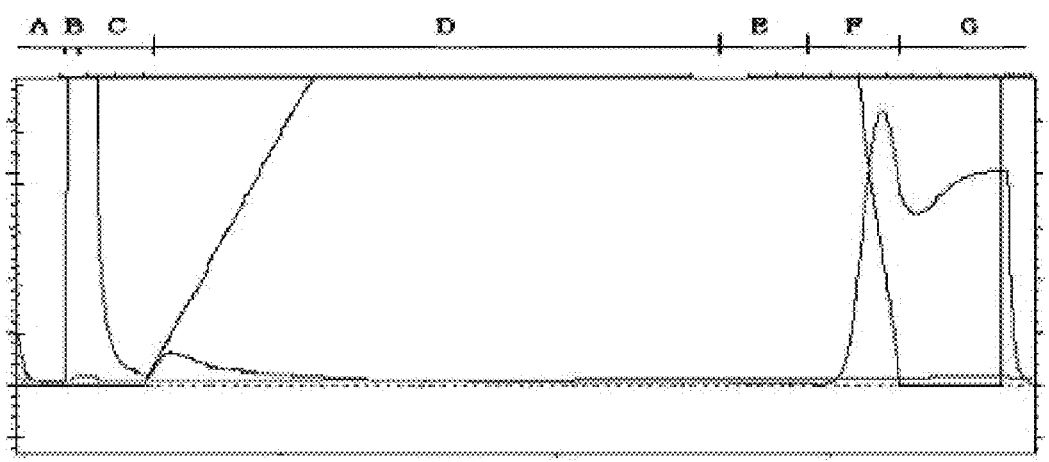
FIG. 1 is a graph showing the result of Fast Protein Purification Liquid Chromatography of the inventive recombinant EC-SOD protein (A: linear equilibrium region, B: sample loading region, C: column washing region, D: refolding region, E: refolding equilibrium region, F: elusion region, G: column washing region, X axis: time and volume (hr:min:sec, mL), Y axis: UV density (Unit)).

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

As used herein, the term "expression vector" describes a vector capable of expressing a target protein or target RNA in a suitable host cell, and refers to a genetic construct comprising essential regulatory elements to which a gene insert is operably linked.

By the term "operably linked", as used herein, it is meant that there is a functional linkage between a nucleotide expression control sequence and a nucleotide sequence encoding a target protein, in such a manner as to perform general functions. For example, a promoter is linked with a nucleotide sequence coding for a protein or RNA, such that it can affect the expression of the coding nucleotide sequence. The operable linkage to a recombinant vector may be prepared using a genetic recombinant technique, and site-specific DNA cleavage and ligation may be carried out using enzymes.

The present disclosure provides a composition for preventing or treating angiogenic diseases, which contains an EC-SOD protein as an active ingredient.

The EC-SOD protein refers to, but is not limited to, a natural or recombinant EC-SOD protein. The natural EC-SOD protein is may be derived from, but is not limited to, mice or humans. The natural EC-SOD protein may have, but is not limited to, amino acid sequences of SEQ ID NO: 3 or SEQ ID NO: 5, and according to some embodiments may be an amino acid sequence of SEQ ID NO: 3. The recombinant EC-SOD protein is not specifically limited, as long as it is prepared from the natural EC-SOD protein, so as to maintain the activity thereof. According to some embodiments, the recombinant EC-SOD protein has an amino acid sequence.

In another aspect, the present disclosure provides a composition for preventing or treating angiogenesis-mediated diseases, which contains, as an active ingredient, a vector having a polynucleotide encoding the EC-SOD protein.

The polynucleotide encoding the EC-SOD protein refers to a polynucleotide capable of encoding the natural EC-SOD protein or the recombinant EC-SOD protein and according to some embodiments, has a base sequence selected from the group that includes, but is not limited to, SEQ ID NO: 2, SEQ ID NO: 4, and SEQ ID NO: 6.

In one Example of the present disclosure, mice overexpressing mouse EC-SOD were prepared according to a method (see Test Example 1), and were irradiated with UVB, and then the morphological change in the tissue thereof was compared with that of wild-type mice. As a result, it was observed that, in the wild-type mice, angiogenesis was induced by UVB irradiation, but in the EC-SOD-overexpressed mice, angiogenesis was significantly inhibited by UVB irradiation (see Example 2-1).

In other Examples of the present disclosure, the expression levels of vascular endothelial growth factor (VEGF) and MMP-9 in the EC-SOD-overexpressing mice by UV light irradiation were examined using Western blot (Example 2-2), an immunohistochemical method (Example 2-3) and a zymography method (Example 2-4). As a result, it could be observed that, in the wild-type mice, the expressions of VEGF and MMP-9 were increased due to UV light irradiation, but in the EC-SOD-overexpressed mice, the expressions of VEGF and MMP-9 were significantly inhibited. The above experimental results suggest that EC-SOD inhibits the expression of VEGF inducing angiogenesis is and inhibits the expression of MMP-9 regulating angiogenesis, thus inhibiting angiogenesis.

In still other examples of the present disclosure, recombinant EC-SOD, from which a heparin-binding domain has been removed, was expressed in *E. coli*, and then isolated from the *E. coli* strain, thus producing a refolded and purified EC-SOD protein (see Example 1), and whether the produced protein would inhibit angiogenesis was examined (see Example 3). As a result, it could be seen that the expression of VEGF was induced by UV light irradiation, but treatment with the recombinant EC-SOD protein resulted in inhibition of the expression of VEGF.

Accordingly, the EC-SOD protein or the vector having inserted therein the polynucleotide encoding the EC-SOD protein can be effectively used to prevent and treat angiogenesis-mediated diseases. The angiogenesis-mediated diseases include all diseases induced by the expression of VEGF (vascular endothelial growth factor) and the expression of MMP (matrix metalloproteinase)-9, and examples thereof may include, are not limited to, cancer, diabetes, rheumatoid arthritis, arteriosclerosis, hemangioma, angiofibroma, diabetic retinopathy, retinopathy of prematurity, neovascular glaucoma, corneal diseases caused by angiogenesis, degenerative spots, macular degeneration, pterygium, retinal degeneration, retrolental fibroplasia, Granular conjunctivitis, telangiectasia, pyogenic granuloma and acne (*Ophthalmol* 102, 1261-1262, 1995; *J Am Acad Derm* 34(3):486-497, 1996; *Circulation* 93(4):632-682, 1996; *Cell* 86: 353-364, 1996).

In still another aspect, the present disclosure provides a method for treating an angiogenesis-mediated eye disease, comprising administering to a subject in need thereof an effective amount of an EC-SOD protein or a vector having a polynucleotide encoding an EC-SOD protein.

In some embodiments, the EC-SOD protein comprises an amino acid sequence of SEQ ID NO: 1 or 3.

As used herein, the term "the angiogenesis-mediated eye disease" includes, but is not limited to, diabetic retinopathy, retinopathy of prematurity, neovascular glaucoma, corneal diseases caused by angiogenesis, degenerative spots, macular degeneration, pterygium, retinal degeneration, retrolental fibroplasia, Granular conjunctivitis, wet type macular degeneration, choroidal neovascularization and corneal graft rejection.

In another aspect, the present disclosure provides a composition for preventing or treating allergic diseases, which contains the EC-SOD protein as an active ingredient.

As described above, the EC-SOD protein refers to, but is not limited to, a natural or recombinant EC-SOD protein. The natural EC-SOD protein is generally derived from, but is not limited to, mice or humans, and according to some embodiments, from humans. The natural EC-SOD protein generally has an amino acid sequence of, but is not limited to, SEQ ID NO: 3 or SEQ ID NO: 5. The recombinant EC-SOD protein is not specifically limited, as long as it is prepared from the natural EC-SOD protein using recombinant technology and maintains the activity thereof. According to some embodiments, the recombinant EC-SOD protein has an amino acid sequence of SEQ ID NO: 1.

In still another aspect, the present disclosure provides a composition for preventing or treating allergic diseases, which contains, as an active ingredient, a vector having inserted therein a polynucleotide encoding the EC-SOD protein.

As described above, the polynucleotide encoding the EC-SOD protein refers to a polynucleotide capable of encoding the natural EC-SOD protein or the recombinant EC-SOD protein, and generally has a base sequence selected from, but is not limited to, the group that includes SEQ ID NO: 2, SEQ ID NO: 4, and SEQ ID NO: 6.

In one Example of the present disclosure, the effect of the recombinant EC-SOD protein on the proliferation and differentiation of T-cells was analyzed. As a result, it could be seen that the recombinant EC-SOD protein induced the formation of the Th1 cytokine IFN-γ in T cells and inhibited the formation of the Th2 cytokine IL-4. This suggests that the recombinant EC-SOD protein has an effect on the differentiation of T cells, and that it blocks the over-differentiation of Th2 cells causing allergic diseases and inducing the differentiation of Th2 cells into Th1 cells, and thus it can be advantageously used to prevent or treat allergic diseases (see Example 4).

In another Example of the present disclosure, the effect of the natural human protein EC-SOD on the differentiation of T cells was examined. As a result, it could be seen that the EC-SOD protein also blocked the over-differentiation of Th2 cells causing allergic diseases and induced the differentiation into Th1 cells (see Example 5).

In still another Example of the present disclosure, whether the recombinant EC-SOD protein has the effect of inhibiting transcriptional factor activity was examined. As a result, it could be seen that the recombinant EC-SOD protein could inhibit the abnormal activity of NF-κB (see Example 6) and had the effect of reducing the degranulation of human mast cells. Accordingly, in view of the fact that mediators, such as histamine, stored in mast cells, are released due to the degranulation of the mast cells to cause inflammatory reactions such as allergy, it can be seen that the recombinant EC-SOD protein of the present disclosure can be advantageously used to prevent or treat allergies (see Example 7).

Thus, the EC-SOD protein or the vector having inserted therein the polynucleotide encoding the protein will be useful in a composition for preventing or treating allergic disease. The allergy is generally selected from allergic asthma, allergic rhinitis, allergic otitis media, anaphylatic shock, allergic skin disease, atopic dermatitis, psoriasis, contact allergic dermatitis and urticaria.

The EC-SOD proteins which are comprised in the inventive composition may include proteins having equivalent physiological activities. The proteins with equivalent physiological activities may include functional equivalents of EC-SOD proteins as well as functional derivatives.

The term "functional equivalents" in the disclosure refer to polypeptides which have equivalent physiological activities with the EC-SOD of SEQ ID NO: 3.

The term "equivalent physiological activities" refer to the activities of inhibiting angiogenesis or allergy. The functional equivalents may polypeptides which show at least 70% amino acid sequence homology with the amino acid sequence of SEQ ID NO: 3, at least 80%, or 90%. The term functional equivalents refer to peptides which have at least 70% amino acid sequence homology (i.e., identity) with the peptides produced by as a result of addition, substitution or deletion of SEQ ID NO: 3, at least 80%, or 90%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% and exhibit substantially identical physiological activity to the polypeptide of SEQ ID NO: 3. Sequence identity or homology is defined herein as the percentage of amino acid residues in the candidate sequence that are identical with amino acid sequence of SEQ ID NO: 3, after aligning the sequences and introducing gaps. If necessary, to achieve the maximum percent sequence identity, any conservative substitutions is not considered as part of the sequence identity. None of N-terminal, C-terminal, or internal extensions, deletions, or insertions into the amino acid sequence of SEQ ID NO: 3 shall be constructed as affecting sequence identity or homology.

Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a predetermined portion of one or both sequences). The programs provide a default opening penalty and a default gap penalty, and a scoring matrix such as PAM 250 (a standard scoring matrix; Dayhoff et al., in *Atlas of Protein Sequence and Structure*, vol 5, supp. 3, 1978). For example, the percent identity can be calculated as: the total number of identical matches multiplied by 100 and then divided by sum of the length of a longer sequence within the matched span and the number of gaps introduced into longer sequences in order to align the two sequences. The scope of the functional equivalents as used herein encompasses polypeptide derivatives obtained by modifying a part of the chemical structure of the polypeptide while maintaining the basic framework and physiological activity of the polypeptide. For example, this includes structural modifications for altering the stability, storage, volatility or solubility of the polypeptide.

In addition, polynucleotide sequences of the inventive compositions may comprise DNA, cDNA, and RNA sequences. The polynucleotide may comprise the sequence selected from the group that includes SEQ ID NO: 2, 4 and 6. Exemplary embodiments of the compositions may comprise, as an active ingredient, plasmid having the polynucleotide sequence thereto, or expression vectors such as viral vectors. The inventive expression vector may comprise expression control sequence by which EC-SOD protein and cDNA of the EC-SOD are expressed. The polynucleotides are isolated from nature or manufactured by the methods which are known in the art.

The expression control sequence refers to a DNA sequence essential to expression of coding sequence which is operatively linked within a certain host cell. The expression control sequence may comprise promoters for transcription, certain operator sequences for controlling of the transcription, the sequences encoding relevant mRNA ribosomal binding site, and the sequences terminating transcription and translation. For example, the control sequences for prokaryotes may comprise promoter, operator, and ribosomal binding site. The control sequences may comprise promoter, polyadenylated signal and enhancer.

After an expression vector was inserted, it could be introduced into a target cell as a phenotype by infection, transfection and transduction.

Gene introducing method by using plasmid expression vector is the method which introduce plasmid DNA directly into a mammalian cell, and FDA has approved to use for human (Nabel, E. G., et al., *Science*, 249:1285-1288, 1990). Unlike viral vector, a plasmid DNA has advantage in respect of even purification. The acceptable expression plasmids of the disclosure may comprise mammalian expression plasmids that are used in the art. For example, but not limited thereto, pRK5 (European Patent No. 307,247), pSV16B (PCT Publication No. WO91/08291) and pVL1392 (PharMingen). The plasmid expression vector which comprise the nucleic acid could be introduced to a target cell by, but not limited thereto, transient transfection, microinjection, transduction, cell fusion, calcium phosphate precipitation, liposome-mediated transfection, DEAE Dextran-mediated transfection, polybrene-mediated transfection, electroporation, gene gun, and other methods (Wu et al., *J. Bio. Chem.*, 267: 963-967, 1992; Wu and Wu, *J. Bio. Chem.*, 263:14621-14624, 1988).

In addition, the viral vectors which contain the polynucleotide sequence, may comprise, but not limited thereto, retrovirus, adenovirus, herpes virus, avipox virus, and lentivirus and the like. All of the viral genes of the retroviral vectors were deleted or modified, and consequently non-viral proteins of the vectors were produced by the infected cells. The main advantages of the retroviral vectors for gene therapy are to transfer large amount of genes into cloned cells, to integrate genes specifically which are transferred to cellular DNA, and to prevent additional infection after gene transformation (Miller, A. D., *Nature*, 357:455-460, 1992). The retroviral vectors which are approved by the FDA is manufactured by using PA317 amphotrophic retroviral packaging cell (Miller, A. D. and Buttimore, C., *Molec. Cell Biol.*, 6:2895-2902, 1986). For the non-retroviral vectors, there is the adenovirus (Rosenfeld et al., *Cell*, 68:143-155, 1992; Jaffe et al., *Nature Genetics*, 1:372-378, 1992; Lemarchand et al., *Proc. Natl. Acad. Sci. USA*, 89:6482-6486, 1992). The main advantages of the adenovirus are to transfer large molecular DNA fragment (36 kb), and to transfect non-cloned cells with very high titer. In addition, herpes viruses could be used in gene therapy for humans (Wolfe, J. H., et al., *Nature Genetics*, 1:379-384, 1992). The lentivirus is a kind of retrovirus, and it is developed from the modification of the HIV backbone since late 1990's. Unlike to existing retrovirus carriers, the lentivirus is more effective in non-divisional cells as well as divisional cells since its activity does not influenced by cell cycle. Accordingly, even in the cells which divide slowly, such as hematopoietic stem cells, the lentivirus is more effective than other viral carriers, and therefore the studies of the lentivirus as a gene transferring carrier have progressed in the field of gene therapy by using hematopoietic stem cells, and keratinocytes. In addition, other relevant viral vectors may be used.

As used herein, the term "pharmaceutically acceptable" refers to what is physiologically acceptable and, when administered to a human, generally does not cause allergic reactions, such as gastrointestinal disorder and dizziness, or similar reactions thereto.

A pharmaceutically acceptable carrier, for example, carriers for the parenteral or oral preparations may be included. The carriers for the parenteral preparations may comprise lactose, starch, cellulose derivatives, magnesium stearate, stearic acid. In addition, the carriers for the parenteral preparations may comprise water, oil, saline, aqueous glucose and glycol, and stabilizers and preservatives. Examples of the stabilizers may include antioxidant such as sodium hydrogen sulfite, sodium sulfite, and ascorbic acid. Examples of the preservatives may be benzalkonium chloride, methyl- or prophyl-paraben, and chlorobutanol. A list of pharmaceutically acceptable carriers is disclosed in Remington's Pharmaceutical Sciences, 19th ed., Mack Publishing Company, Easton, Pa., 1995.

The protein or a vector having inserted therein a polynucleotide encoding the protein may be prepared by mixing with the pharmaceutically acceptable carriers into various oral or parenteral preparations according to any method. Also, the peptide may be administered by various routes according to any method. Namely, it may be administered by oral or parenteral routes. The injectable preparations, such as isotonic solution or suspension and ointments, are desirable for the parenteral preparations. The injectable preparations may be prepared by using relevant dispersants, wetting agents, or suspending agents according to any method. For example, the compositions may be formulated into injectable compositions by dissolving components into saline or buffers. Furthermore, for oral administration, which are not limited thereto, the composition can be formulated in the form of powder, granule, tablets, pills and capsules, and the like. These preparations may also comprise diluents (e.g., lactose, dextrose, sucrose, mannitol, sorbitol, cellulose and/or glycine), lubricants (e.g., silica, talc, stearic acid and a magnesium or calcium salt thereof, and/or polyethylene glycol) in addition to the active ingredient. Among various preparations, tablets may also comprise binders, such as magnesium aluminum silicate, starch pastes, gelatin, tragacanth, methylcellulose, sodium carboxymethylcellulose and/or polyvinylpyrrolidone, and, if desired, may further comprise disintegrating agents, such as starches, agar or alginic acid or a sodium salt thereof, heterogenous mixtures and/or absorbents, colorants, flavors and sweeteners. The composition may be prepared by mixing, granulization or coating.

The inventive pharmaceutical composition may be administered by various routes, but not limited thereto, according to any biotechnological method, such as by oral, intravenous, intramuscular, intraarterial, intramarrow, subdural, intracardiac, intracutaneous, subcutaneous, intraperitoneal, intranasal, gastrointestinal tracts, parenteral, sublingual or rectal administration.

The pharmaceutical composition may be administered parenterally, by subcutaneous, intravenous, intramuscular, instrajoint, intrabursal, intrasternum, subdural, intralesional, and intracranium, with injection or infusion. For example, an injectable form of the inventive pharmaceutical composition may be administered with a given amount of the formulation by injecting into a subcutaneous layer with a 4-6 mm syringe or lightly pricking the skin with 30-gauge injection needle, namely, the Messo therapy. In addition, an ointment form of the inventive pharmaceutical composition may be administered by a method of applying directly to the skin. The 'intracutaneous' refers to transfer effective amount of an active ingredient which is comprised in the inventive composition by administered into the skin. In some embodiments, the composition whose active ingredient is the EC-SOD protein of the disclosure should be administered directly to the skin. In addition, the composition may be administered by biotechnological methods related to protein transfer.

The compositions may be administered to patients with the amount which is effective for preventing disease. Generally, the effective amount of the inventive composition is about 0.0001 to 100 mg/kg body weight/day. According to some embodiments, 0.01 to 1 mg/kg body weight/day may be administered. It may be suitably determined by considering various factors, such as age, body weight, health condition, sex, disease severity, diet and excretion of a subject in need of treatment, as well as administration time and administration route.

In addition, the present disclosure provides the method for preparing an EC-SOD protein, which comprises:
 (a) cloning the polynucleotide encoding the EC-SOD protein into the expression vector;
 (b) transforming a host cells by introducing the expression vector to the host cells;
 (c) expressing the EC-SOD protein by culturing the transformed host cells;
 (d) collecting the inclusion body of the expressed EC-SOD protein; and
 (e) dissolving the inclusion body, and inducing refolding of the EC-SOD protein.

The step (a) of cloning the polynucleotide encoding the EC-SOD protein into the expression vector can be carried out using a conventional recombinant DNA technique. The polynucleotide encoding the EC-SOD refers to a polynucleotide capable of encoding the natural EC-SOD protein or the recombinant EC-SOD protein and may have a base sequence selected from, but is not limited to, the group that includes SEQ ID NO: 2, SEQ ID NO: 4 and SEQ ID NO: 6. The polynucleotide can be constructed by performing PCR amplification using suitable primers. Alternatively, the DNA sequence may also be synthesized by a standard method, for example, using an automatic DNA synthesizer (commercially available from Biosearch or Applied Biosystems). The expression vector may be a conventional expression vector used in the art and can be suitably selected depending on host cells. For example, when the host cells are *E. coli* cells, a pET28a vector (Novagene, USA) may be used. Because the preparation method of the present disclosure aims to express and produce EC-SOD in large amounts, any expression vector may be suitably selected and used, as long as it can achieve this purpose.

The vectors may comprise, but not limited thereto, plasmid vector, cosmid vector, bacteriophage vector, and viral vector, and the like.

The suitable expression vectors may comprise expression control sequences such as promoter, operator, initiation codon, stop codon, polyadenyated signal and enhancer (stimulating gene) as well as membrane targeting, signal sequence for secretion, leader sequences, and may be manufactured according to a purpose. The promoter may be constitutive or inducible. In addition, the expression vector may comprise selective markers to select the host cells which contain the vector, and if the expression vector is replicable, it may comprise an origin of replication.

The step (b) transforming a host cells by introducing the expression vector to the host cells may comprise any method of introducing nucleic acid to the host cells, and may be performed by transformation techniques. According to some embodiments, the techniques may comprise, but not limited thereto, microprojectile bombardment, electroporation, $CaPO_4$ precipitation, $CaCl_2$ precipitation, PEG-mediated fusion, microinjection, liposome-mediated method, and the like.

In the above cases, the host cells may be prokaryotic or eukaryotic. According to some embodiments, the host cells may comprise, but are not limited to, prokaryotic host cells such as *Escherichia coli, Bacillus subtilis, Streptomyces, Pseudomonas, Proteus mirabilis*, and *Staphylococcus*, and the lower eukaryotes such as the fungi (for example, *Aspergillus*), yeasts (for example, *Pichia pastoris, Saccharomyces cerevisiae, chizosaccharomyces, Neurospora crassa*), higher eukaryotic cells originated from insect cells, plant cells, mammalian cells. According to some embodiments, *Escherichia coli* may be used as a host cell.

The step (c) of expressing the EC-SOD protein by culturing the transformed host cells comprises culturing the host cells in a suitable medium and conditions so as to express the EC-SOD protein in the host cells. The methods of expressing the transformed cells to express the protein in the cells. For example, the expression of the protein can be induced by inoculating the transformed cells in a suitable medium allowing the cells to grow, preculturing the cells, inoculating the precultured cells in a medium, and then culturing the cells in suitable conditions.

Collecting the inclusion body in the step (d) can be carried out using a method for isolating and collecting insoluble inclusion bodies. For example, the inclusion body can be collected from the cell precipitate by centrifugation.

The step (e) of dissolving the inclusion body and inducing the refolding of the inclusion body can be carried out using any conventional method. For example, it can be carried out by dissolving the inclusion body in a buffer solution containing a protein denaturant, adsorbing the solution onto a metal affinity resin column, and inducing the refolding of the inclusion body while reducing the concentration of the denaturant.

For example, dissolving the inclusion body and inducing the refolding of the inclusion body can be performed by dissolving the inclusion body in a Tris buffer solution (8 M urea, 50 mM Tris-Cl, 100 mM NaCl) containing 8M urea as a denaturant, adsorbing the solution onto a metal affinity resin-packed column, and slowly removing the urea while applying a concentration gradient to the column using a Tris buffer containing 1 M urea, thus inducing the refolding of the inclusion body. Then, a pure refolded protein can be obtained by allowing either an elution buffer solution showing strong adsorption onto the column, or an elution buffer solution having a low pH value (generally less than 4), to flow from the column top downward so as to flow out through the column bottom. For example, the pure refolded protein can be obtained by allowing an imidazole (generally 1M)-containing elution buffer solution having strong adsorption onto a metal affinity chromatography column, to flow from the column top downward so as to flow out through the column bottom. In order to increase the yield of the protein, it is possible to feed the elution buffer solution into the column in such a manner that it has a concentration gradually increasing with the passage of time, that is, it has a concentration gradient.

The method for preparing the EC-SOD protein may additionally comprise a step (f) of separating and purifying the EC-SOD by using a gel-filtration column. Then, various isolation and purification processes, including additional purification, concentration and solvent exchange, may be carried out depending on the intended use. For example, the resulting EC-SOD protein can be subjected to techniques, such as salting-out (e.g., ammonium sulfate precipitation and sodium phosphate precipitation), solvent precipitation (a protein fractionation precipitation method using acetone, ethanol, or the like), dialysis, gel filtration, ion exchange, ion exchange chromatography, reverse phase chromatography and affinity chromatography, alone or in combination, to purify the EC-SOD protein.

The standard recombinant DNA and molecular cloning techniques are described in the following references (Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)).

As described above, a vector having inserted therein a polynucleotide encoding the EC-SOD protein could be administered to an individual with effective amount, and prevent or treat diseases caused by angiogenesis or allergic diseases. In addition, the vector may be used for preparation a therapeutic agent for angiogenesis-mediated diseases or allergic diseases.

As mentioned above, an EC-SOD protein or a vector having a polynucleotide encoding the EC-SOD protein has the effect on inhibiting angiogenesis by inhibiting the expression of VEGF and MMP-9 which induce angiogenesis. Therefore, the EC-SOD protein or the vector may be useful for preventing or treating angiogenesis-mediated diseases. And the EC-SOD protein or the vector having a polynucleotide encoding the EC-SOD protein also has the effects of inhibiting over-differentiation of Th2 cells which cause allergic diseases, inhibiting transcription factor (NF-κB), and reducing degranulation of human mast cells. Accordingly, the EC-SOD protein or the vector may be useful for preventing or treating allergy diseases. In addition, the inventive method for preparing an EC-SOD protein may be used in preparing an EC-SOD protein having the activity on a large scale. Therefore, the inventive method may be useful industrially.

Hereinafter, the present disclosure will be described in detail by reference to the following examples. It is to be understood, however, that these examples are for illustrative purpose only and are not constructed to limit the scope of the present disclosure.

Test Example 1

Preparation of Mice Overexpressing EC-SOD

First, mice overexpressing mouse EC-SOD were prepared in the following manner. The base sequence and amino acid sequence of the mouse EC-SOD are set forth in SEQ ID NO: 5 and SEQ ID NO: 6, respectively.

As wild-type BDF1 mice, 8-10-week-old BDF1 mice (Central Laboratory Animal Inc., Korea) were used. The EC-SOD-overexpressing mice were prepared according to a method using the 8-10-week-old BDF1 mice (H. Y. Ha. et. al., *Biochem Biophys Res Commun,* 348: 450-458, 2006). In the experiment, the animals were used under the approval of the Catholic Institute, The Catholic University of Korea.

Specifically, hybrid mice (C57BL/6×CBA F1) were purchased from the Korea Research Institute of Bioscience and Biotechnology. To induce superovulation, 5 IU of each of pregnant mare's serum gonadotropin (PMSG) and human chorionic gonadotropin (hCG) were injected intraperitoneally into the female mice, at an interval of 48 hours, and then mated with the same line of male mice at a 1:1 ratio. The next morning, the presence or absence of a vaginal plug in the animals was observed, and only an individual having the vaginal plug was butchered, from which an oviduct was taken. From the oviduct ampulla, embryos were collected. As a culture medium, 0.4% BSA-containing M16 culture medium was used.

In order to obtain mice where the skin tissue-overexpression of EC-SOD had been induced, the mouse EC-SOD cDNA in a pCRII TOPO vector (provided by professor Suh Jun-Gyo, College of Medicine, Hallym University) containing mouse EC-SOD cDNA (SEQ ID NO: 6) was digested with restriction enzymes and inserted into a pBS KS vector containing a human keratin K14 promoter. Also, the vector was inserted with chicken ovalbumin poly (A) to facilitate expression in vitro. In order to inject DNA into the embryos, the expression vector was cut with restriction enzymes Hind and XhoI. The DNA cut with the restriction enzymes was electrophoresed on 1% agarose gel, recovered by dialysis, and then isolated and purified with phenol-chloroform. It was dialyzed in 10 mM Tris (pH 7.4)/0.2 mM EDTA) to a final concentration of 4 ng/l. The foreign gene-containing DNA solution was injected into the pro-nuclei of one-cell-stage embryos. The embryos injected with the foreign gene were cultured to the two-cell stage, and healthy embryos were selected from the cultured embryos. Female ICR mice in heat were mated with male mice, and next day, the presence or absence of a vaginal plug was observed, and a mouse having the vaginal plug was used as a surrogate mother. About 15-20 embryos well grown to the two-cell stage were collected and transplanted into the oviduct ampulla of the pseudopregnant recipients, after which a muscular layer and an epidermal layer were sutured to each other. After the transplantation, born animals were grown for about 3 weeks. Next, their tails were cut about 1 cm and treated with lysis buffer at 55° C., and phenol was added thereto to extract genomic DNA. The genomic DNA was PCR-amplified with the following primer set so that whether it had been transformed or not was examined. The PCR amplification was performed in the following conditions: predenaturation at 94° C., 30 cycles of 30 sec., at 94° C., 30 sec. at 51° C. and 45 sec. at 72.5° C., and then final extension at 72.5° C. for 5 min.

```
Sense primer
                                    (SEQ ID NO: 7)
5'-TTG TCT CTA ATA GAG GGT C-3'

Ati-sense primer
                                    (SEQ ID NO: 8)
5'-TA AGC CTG TCT ATC TTC T-3'
```

Mie overexpressing human EC-SOD were obtained from the National Jewish Medical & Research Center (Colorado, USA; Oury et al. JBC 268 (21): 15394, 1993).

Example 1

Preparation of Recombinant EC-SOD Protein Having Biological Activity

<1-1> Cloning of Fusion EC-SOD Gene for Expression of Recombinant EC-SOD Protein In order to prepare a recombinant EC-SOD protein having biological activity, recombinant EC-SOD, that includes 209 amino acids and containing deletion of the signal peptide at the N-terminal end of human EC-SOD and deletion of 13 amino acids at the C-terminal end, was cloned in the following manner. The base sequence and amino acid sequence of the recombinant EC-SOD are set forth in SEQ ID NO: 2 and SEQ ID NO: 1, respectively, and the base sequence and amino acid sequence of the human EC-SOD are set forth in SEQ ID NO: 4 and SEQ ID NO: 3, respectively.

A pUC 18-hEC-SOD vector (provided by Professor Marklund, Clinical Chemistry, Sweden) containing human EC-SOD cDNA (SEQ ID NO: 4), as a template, was amplified by PCR using the following primers, thus preparing human EC-SOD cDNA:

```
Sense primer
                                    (SEQ ID NO: 9)
5'-tagattctggacgggcgagga-3'

Anti-sense primer
                                    (SEQ ID NO: 10)
5'-tactcgagtcactctgagtgct-3'
```

The PCR amplification was performed using PfuI polymerase in the following conditions: predenaturation at 95° C. for 5 min, and then 30 cycles of 30 sec at 95° C., 30 sec at 55° C. and 1 min at 72° C., followed by final extension at 72° C. for 5 min. The amplified gene product was digested with restriction enzymes EcoRI and XhoI, and then ligated into a pET28a vector (NovaGene, USA), digested with the same restriction enzymes, using T4 ligase at 4° C. for 12 hours.

The vector was transfected into *E. coli* DH5a, and then the transformants were cultured in LB solid medium containing 25 mg/mL of kanamycin, and the cultured transformants were screened. Whether the EC-SOD gene had been correctly inserted into the screened transformants was examined by gene sequence analysis. From the transformants determined to have the recombinant EC-SOD gene inserted therein, a vector was isolated. The vector was inserted into host cell *E. coli* BL21 (NovaGene, USA) for overexpression, and the cells were cultured in LB solid medium containing 25 mg/mL of kanamycin, while a strain overexpressing the EC-SOD protein was screened.

<1-2> Expression of Recombinant EC-SOD Protein

The strain screened in Example 1-1 was cultured in LB liquid medium, containing 25 mg/mL of kanamycin, at 37° C. When the cells reached an OD (optical density) Of 0.6 at 600 nm, IPTG (1 mM) was added thereto to induce the expression of the EC-SOD protein, and the cells were cultured at 37° C. for 6 hours, thus expressing the recombinant EC-SOD protein in the cells.

<1-3> Induction of Refolding and Purification of Recombinant EC-SOD Protein

After the completion of the expression, the cells were collected from the culture medium by centrifugation, and the collected cells were suspended in 50 mM Tris buffer (pH 7.5) containing 100 mM calcium chloride and were disrupted with an ultrasonic disruptor. The cell suspension was centrifuged, and the precipitate layer was isolated and washed three times with 50 mM Tris buffer containing 100 mM calcium chloride. The washed cell precipitate contained an insoluble protein inclusion body. 10 mg of the washed inclusion body (a fusion protein content of 50%) was added to Tris buffer solution (50 mM Tris-Cl, 100 mM NaCl, pH 7.5), and then dissolved by the addition of 8M urea. After the inclusion body was completely suspended at room temperature for 2 hours, it was subjected to phase separation by centrifugation. The upper aqueous layer was collected because it contained the dissolved recombinant EC-SOD protein inclusion body (inclusion body solution).

The refolding and purification of the recombinant EC-SOD protein were performed in the following manner using fast protein purification liquid chromatography (FPLC). The buffer solution (8 M urea, 50 mM Tris-Cl, 100 mM NaCl, pH 7.5) was introduced into a metal affinity resin-packed chromatography column (5 ml His Trap FF crude, GE Healthcare, USA) at a flow rate of 1 ml/min to equilibrate the column, and then 5 ml of the above-obtained inclusion body solution was injected downward into the top of the metal affinity resin-packed chromatography column (3 ml) at a flow rate of 1 mL/min, so that the folded protein was adsorbed onto the solid matrix in the column.

After the completion of the injection, 50 ml of the buffer solution was injected downward into the top of the column at a flow rate of 1 mL/min in order to remove non-absorbed solids. After cell debris was completely removed from the column as described above, a Tris buffer solution (50 mM Tris buffer, 1 M urea, 100 mM NaCl, 100 mM $ZnCl_2$, 50 mM $CuSO_4$, pH 7.5), containing 1 M urea and comprising Zn and Cu atoms having an effect on the activity of EC-SOD, was injected downward into the top of the column at a flow rate of 0.5 mL/min, while applying a linear concentration gradient, thus gradually reducing the concentration of the denaturant in the column. Accordingly, the metal ions (Zn and Cu) were completely substituted into the target protein with the natural three-dimensional structure, and thus the folded protein adsorbed onto the solid matrix was refolded to have activity.

Then, a Tris buffer solution, containing 2M imidazole and 1M urea, was fed downward into the top of the column with a concentration gradient. The refolded fusion protein was eluded when an elution buffer solution having an imidazole concentration of 0.5M was fed into the column (see FIG. 1).

<1-4> Separation and Purification of Recombinant EC-SOD Protein

In order to remove a large amount of imidazole from the eluted protein obtained in Example 1-3, completely refold the protein and separate the protein according to size, a fast protein purification liquid chromatography (FPLC) column and a gel filtration chromatography column (Sepharose 12 column) were used. In this process, a Tris buffer solution (50 mM Tris-Cl, 100 mM NaCl, pH 7.5) or a phosphate buffered saline (pH 7.5) was injected downward into the top of the column at a flow rate of 0.5 mL/min to separate and purify the protein. The separated target protein was concentrated by ultrafiltration.

Figure 2:
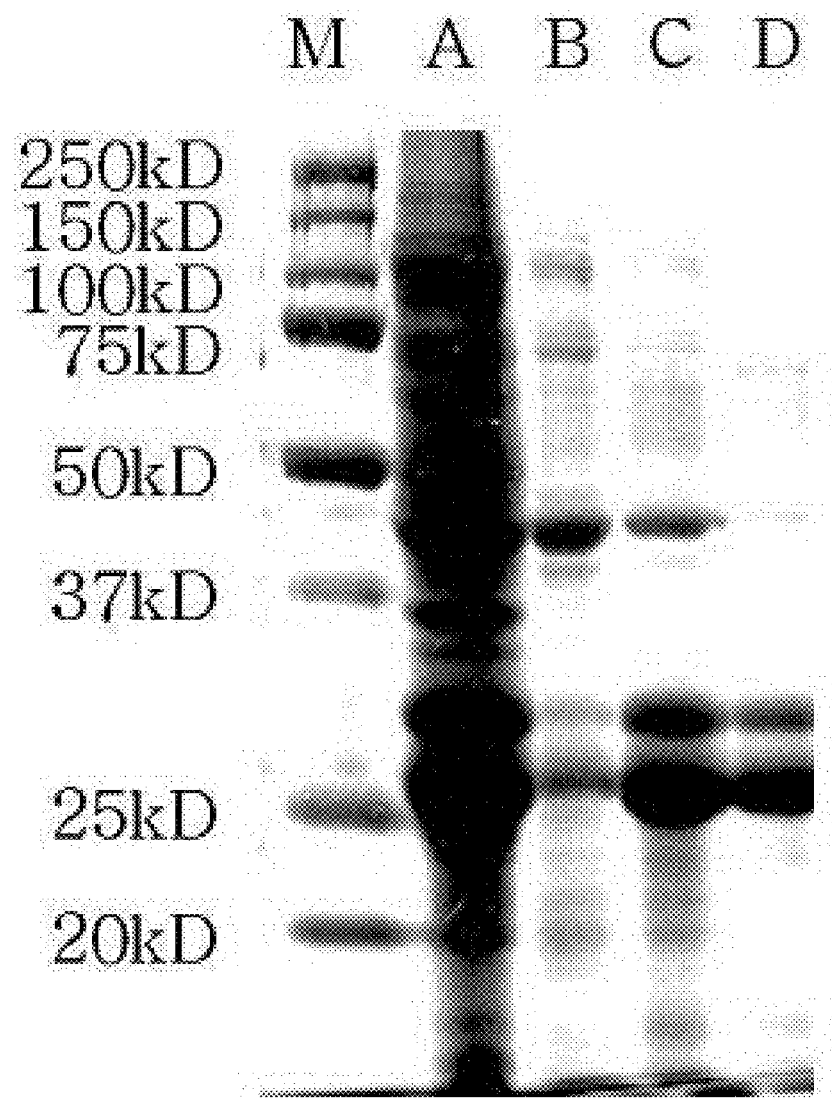
FIG. 2 is a photograph of Coomassie-blue protein staining showing the SDS-PAGE result of the inventive recombinant EC-SOD protein which is refolded and purified (M: molecular size marker, A: inclusion body which is diluted with 8M urea buffer (before refolding purification), B: inclusion body impurity which is not attached in the column and eluted, C: eluted EC-SOD after refolding purification, D: concentrated EC-SOD by ultrafiltration after desalting purification).

As a result, the recombinant EC-SOD protein of the present disclosure could be obtained. Also, the sample in each purification step was analyzed by SDS-PAGE and, as a result, as can be seen in FIG. 2, the recombinant EC-SOD protein was well separated.

<1-5> Identification of EC-SOD Protein by Western Blot

In order to examine whether the recombinant EC-SOD protein separated and purified in Example 1-4 was rightly EC-SOD, Western blot analysis was performed. As the standard protein of EC-SOD, human EC-SOD expressed by human keratinocyte HaCaT cells (provided by Professor N. Fusenig, Cancer Research, Germany) was used. The human EC-SOD, expressed by HaCaT cells, and the EC-SOD proteins, separated and purified in Example 1-4, were separated by electrophoresis in 10% polyacrylamide gel, and then transferred to a polyvinylidene fluoride membrane (Gelman Laboratory, MI, USA). Then, the polyvinylidene fluoride membrane was blocked with 5% skimmed milk and cultured with an anti-EC-SOD polyclonal antibody (1:500, Santa Cruz, USA). The membrane was washed with water, incubated with peroxidase-conjugated secondary antibody IgG (Santa Cruz, USA), washed again with water, and then color-developed using an ECL detection kit (GE Healthcare, USA) according to the manufacturer's instruction.

Figure 3:
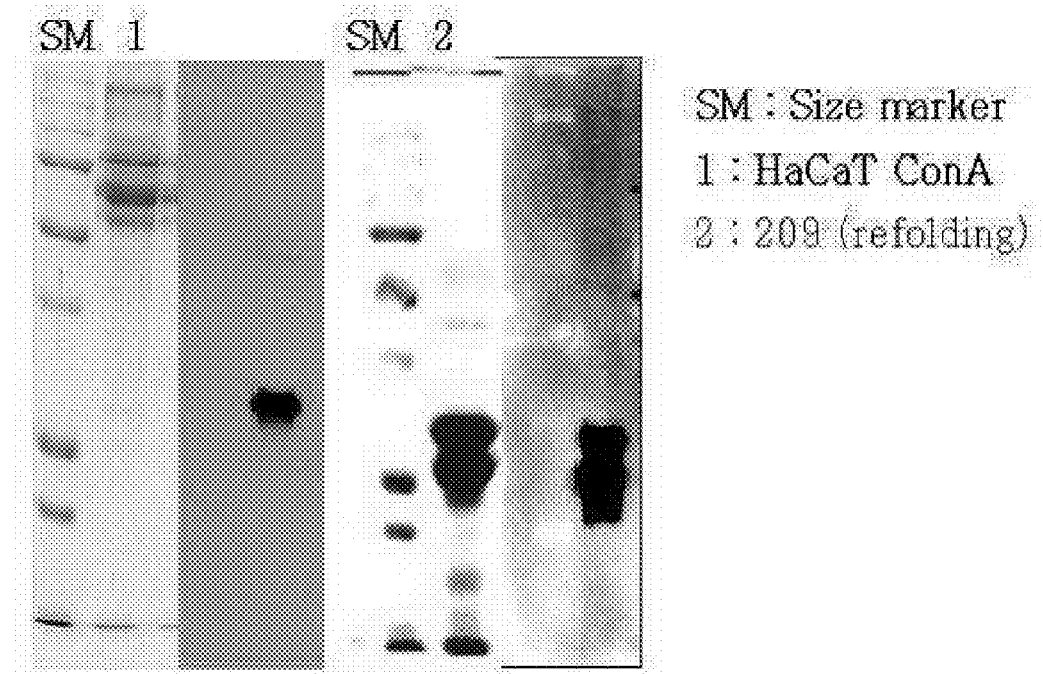
FIG. 3 is a western blot result of recombinant EC-SOD protein by using anti-EC-SOD protein antibody (SM: size marker, 1: control (HaCaT human EC-SOD), 2: inventive recombinant EC-SOD protein).

As a result, as can be seen in FIG. 3, a positive response was shown in the human EC-SOD (lane 1) and also detected in the separated and purified recombinant EC-SOD protein (lane 2). This suggests that the purified protein was human EC-SOD.

<1-6> Examination of Activity of Recombinant EC-SOD Protein

In order to examine whether the separated and purified recombinant EC-SOD protein has the biological activity of SOD, the activity of the recombinant EC-SOD protein was tested using an SOD assay kit-WST (Dojindo Molecular Technology, USA) according to the manufacturer's instruction.

Figure 4:
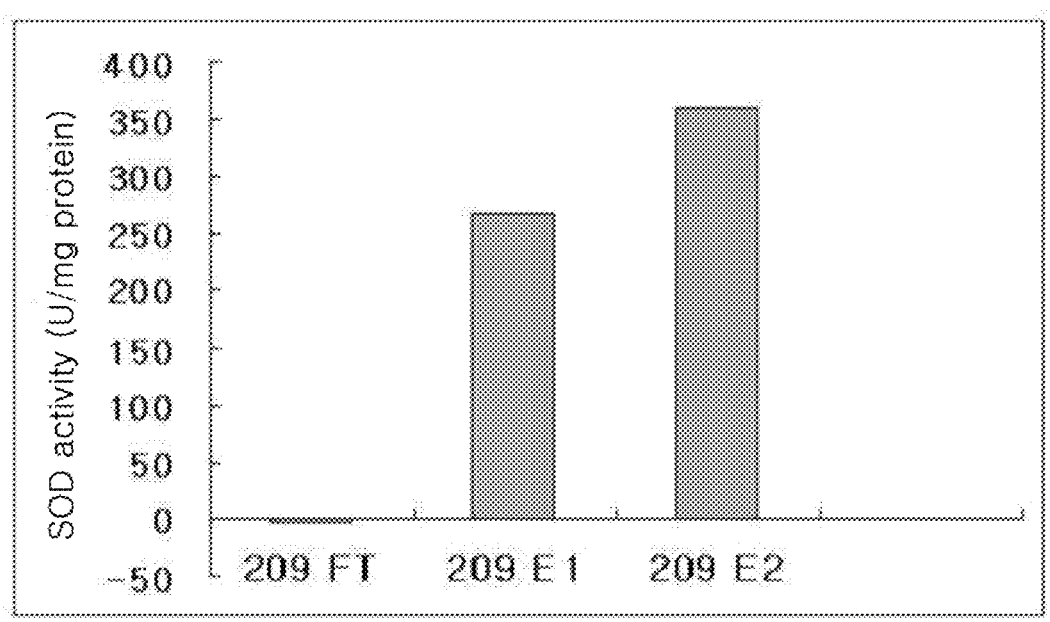
FIG. 4 is a graph of EC-SOD activity during purification step (209 FT: eluted but not attached sample during purification 209 E1: primary purified recombinant EC-SOD protein refolded by metal affinity chromatography, 209 E2: isolated and purified recombinant EC-SOD protein by gel-filtration column).

As a result, as can be seen in FIG. 4, the sample (209FT) eluted without being adsorbed in the purification process showed no activity, the primarily purified recombinant EC-SOD protein (209 E1) refolded using the metal affinity chromatography column showed an activity of 250 unit/mg protein, and the recombinant EC-SOD protein (209 E2) separated and purified using the gel-filtration column showed an activity of 360 unit/mg protein.

<1-7> Examination of ROS Removal Effect of Separated and Purified Recombinant EC-SOD Protein In order to examine the ROS (reactive oxygen species) removal effect of the recombinant EC-SOD protein in HaCaT cells, the recombinant EC-SOD protein, separated and purified in Example 1-4, was treated in the following manner.

Skin keratinocyte HaCaT cells were plated on 18-mm cover slips at a concentration of $1 \times 10^4$ cells/cover slip, and then cultured in an IMDM medium (Isocove's modified Dulbecco's medium, GIBCO), containing 10% fetal bovine serum (FBS, GIBCO) and 1% of 100 units penicillin and 100 g streptomycin/ml of medium in 5% $CO_2$ at 37° C. When the adhered cells reached a confluence of about 30-40%, the fetal bovine serum was removed, and then the cells were cultured. When the cells reached a confluence of 50-60%, the cells were pretreated with 10 μg of the EC-SOD protein. After the cells were irradiated with UVB at a dose of 100 J/m² for 3 hours, the cells were allowed to react with 10 mM DCFH-DA at 37° C. for 30 minutes and observed with a fluorescent microscope. The fluorescent micrograph was obtained using a Zeiss digital camera.

Figure 5:
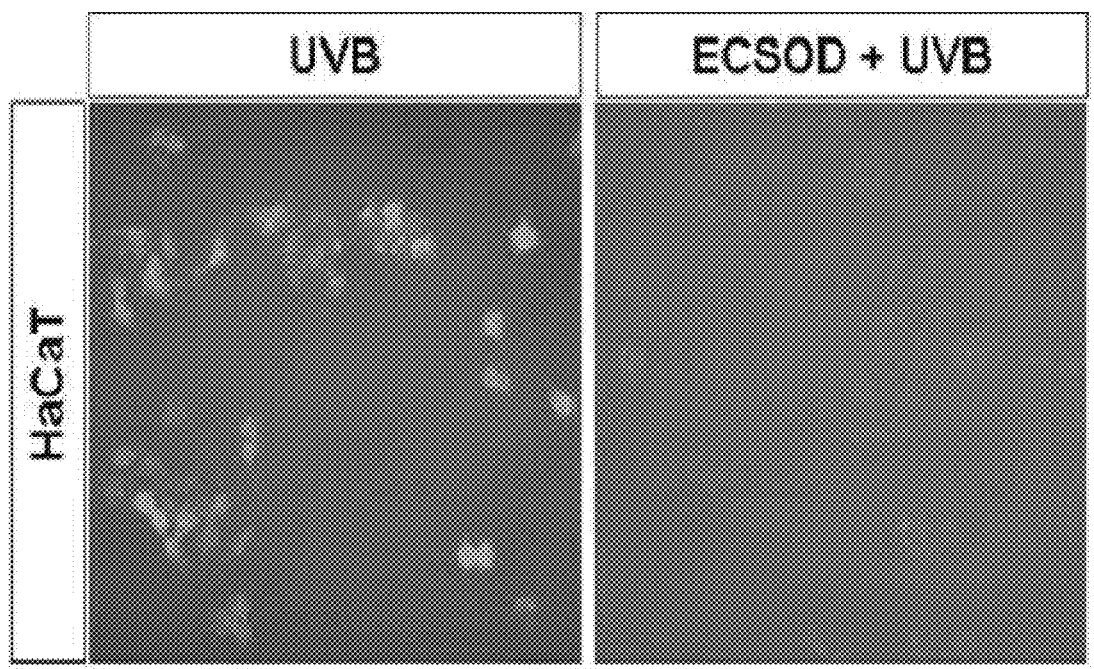
FIG. 5 is a photograph showing inhibition activity of recombinant EC-SOD protein from ROS caused by UVB in the HaCaT cell (UVB: UVB irradiation only, EC-SOD+ UVB: UVB irradiation and EC-SOD treatment).

As a result, as can be seen in FIG. 5, in the UVB group where the cells were irradiated only with UVB, ROS was not removed, but in the EC-SOD+UVB group where the cells were irradiated with UVB and treated with the inventive recombinant EC-SOD protein, ROS was effectively removed.

Example 2

Angiogenesis Inhibitory Effect of Natural EC-SOD Protein

<2-1> Morphological Comparison of EC-SOD-Expressing Mice with Wild-Type Mice

The back skin of each of the mouse EC-SOD-overexpressing mice, prepared in Test Example 1, and wild-type BDF1 mice, was irradiated four times with UVB at a dose of 2 kJ/m² at 24-hr intervals. Specifically, the back skin of each mouse was shaved at 2 days before UVB irradiation, and twenty-four 8-week-old mice were irradiated with UVB at a dose of 200 mJ/cm² using 6 UVB lamps (FS24T12/UVB/HO, 290-320 nm, Voltare, Fairfield, Conn., USA) having the highest energy at 305 nm in a wavelength range from 280 nm to 340 nm. During the UVB irradiation, the height of the lamps was controlled such that the surface of the back skin of each of the anesthetized mice was irradiated with a dose of 0.3 mW/cm². The mice of each group (n=6) were irradiated four times with UVB at 24-hr intervals, and at 1 hour after the $4^{th}$ UVB irradiation, the mice were sacrificed for experiments. The back skin of each of the sacrificed mice was incised and visually observed, and the observation results are shown in FIGS. 6A to 6D.

Figure 6A:
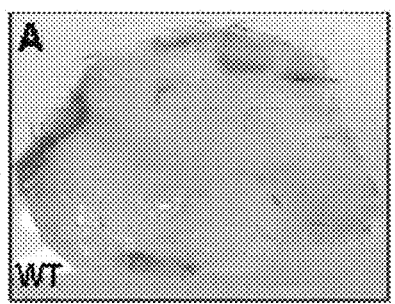
FIGS. 6A-6D are photographs showing morphological changes in skins of mice by UV irradiation.
Figure 6B:
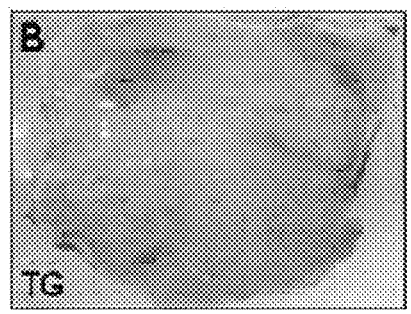
Figure 6C:
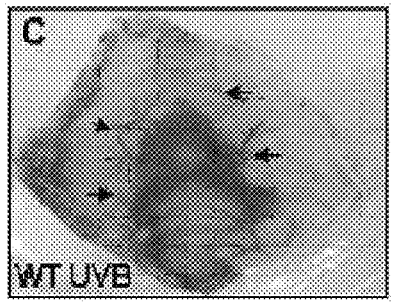
Figure 6D:
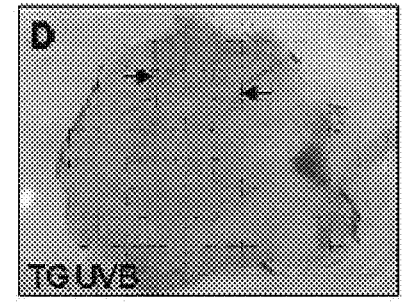

As can be seen in FIGS. 6A to 6D, in the case where the wild-type mice were irradiated with UVB (FIG. 6C), angiogenesis, a skin inflammatory reaction and erythema were significantly induced compared to the case where the mice were not irradiated with UVB (FIG. 6A). However, in the EC-SOD-overexpressing mice, there was no statistically significant difference between before UVB irradiation (FIG. 6B) and after UVB irradiation (FIG. 6D). In other words, it could be observed that angiogenesis induced by UV light (UVB) irradiation in the wild-type mice (FIG. 6B) was significantly inhibited in the EC-SOD-overexpressing mice (FIG. 6D). These results suggest that the EC-SOD protein inhibits angiogenesis.

<2-2> Western Blot

The expression level of angiogenesis-inducing vascular endothelial growth factor (VEGF) in the mouse EC-SOD-overexpressing mice prepared in Test Example 1 was analyzed by Western blot.

The back skin tissues or cells of each of the EC-SOD-overexpressing mice, sacrificed in Example 2-1, and the wild-type mice, were homogenized and extracted with an extraction solution (50 mM Tris HCl pH 8.0, 5 mM EDTA, 150 mM NaCl, 0.5% sodium deoxycholate, 1% Nonidet P-40, 0.1% SDS, 1 mM PMSF, 1 mM NaF, 1 mM $NaVO_4$, and a protease inhibitor cocktail (Roche, Germany)). To determine protein concentration, a bio-rad protein kit (Bio-Rad, CA, USA) was used, and bovine serum albumin (BSA) was used as a standard material. The protein extracts were separated on 10% polyacrylamide gel, and then transferred to a polyvinylidene fluoride membrane (Gelman Laboratory, MI, USA). Then, the polyvinylidene fluoride membrane was blocked with 5% skimmed milk, and then incubated with each of an anti-VEGF polyclonal antibody (1:500, Santa Cruz, USA) and an anti-beta-actin antibody. The membrane was washed with water, incubated with peroxidase-conjugated secondary antibody IgG (Santa Cruz, USA), washed again with water, and then color-developed with an ECL detection kit.

Figure 7:
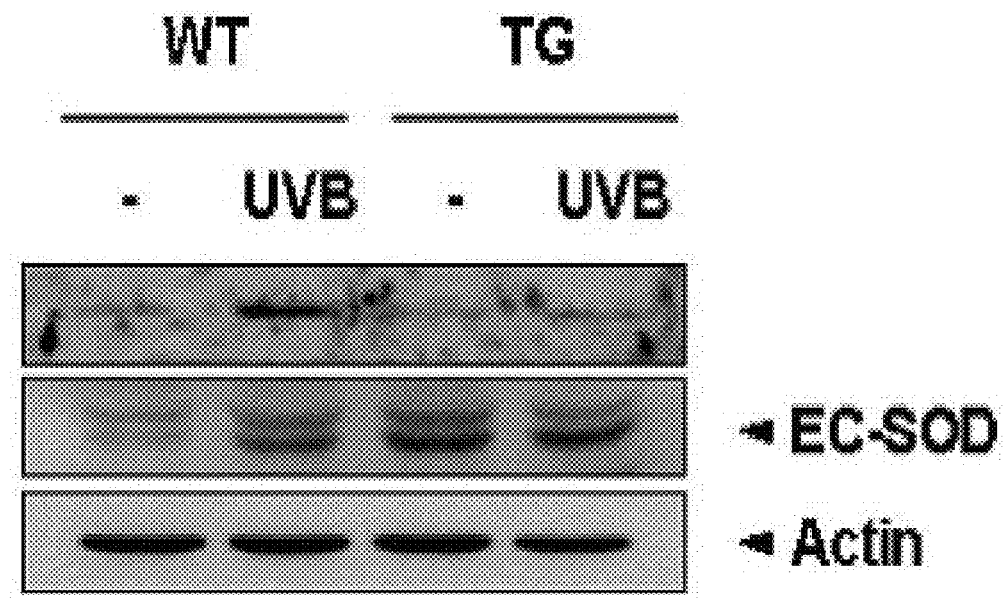
FIG. 7 is a western blot result of VEGF expression in UV irradiated mouse tissue. Actin was used as loading control (WT: wild type mouse, TG: EC-SOD overexpressed mouse).
Figure 8A:
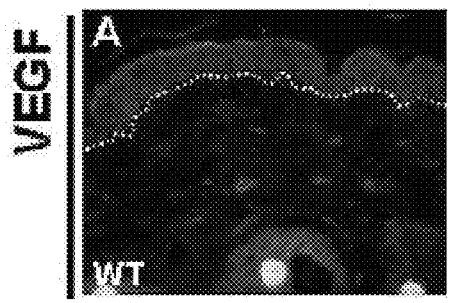
FIGS. 8A-8D are photographs showing VEGF expression of UV irradiated mouse by using an immunohistological method.
Figure 8B:
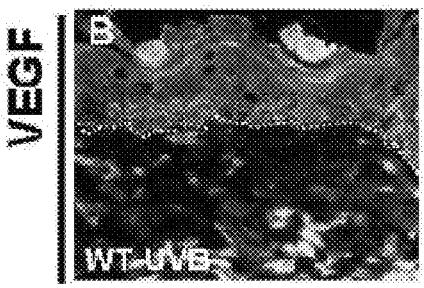
Figure 8C:
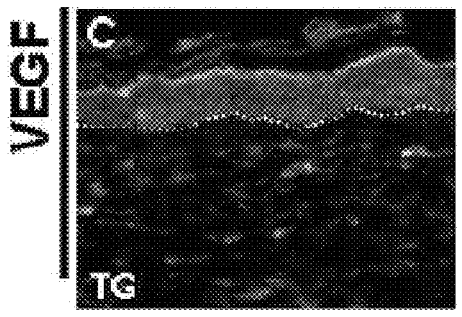
Figure 8D:
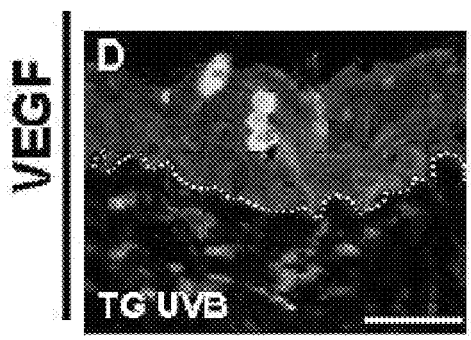

As a result, as can be seen in FIG. 7, the expression level of VEGF in the wild-type mice was increased due to UVB irradiation, but the expression of VEGF in the EC-SOD-overexpressed mice irradiated with UVB was significantly reduced. These results confirm again that the EC-SOD protein has the effect of inhibiting angiogenesis.

<2-3> Immunohistochemical Examination

Whether EC-SOD inhibits the expression of VEGF was examined again by an immunohistochemical method.

The back skin tissue of each of the EC-SOD-overexpressing mice, sacrificed in Example 2-1, and the wild-type mice, was fixed with 4% paraformaldehyde in 0.5M phosphate buffered saline (pH 7.4). The fixed tissue was washed with running water, dehydrated with ethanol, embedded in paraffin, sectioned to a thickness of 5 mm and attached to glass slides. The sections were deparaffinized with xylene solution, hydrated with ethanol, and then stained with hematoxylin and eosin. The deparaffinized tissue segments were blocked by treatment with 3% hydrogen peroxide solution. To reduce nonspecific binding and background staining, the sections were treated with 10% goat serum. Each of the tissue slides was treated with an anti-VEGF polyclonal antibody (1:500, Santa Cruz, USA) and visualized by the avidin-biotin-immunoperoxidase complex method using a streptavidin-biotin kit (LSAB, Dako, Calif., USA). The stained tissue was washed with water, and then color-developed with diaminobenzidine (DAB), and the tissue sections were counterstained with 0.2% Mayer's hematoxylin (Sigma, MO, USA). The staining results are shown in FIGS. 8A to 8D.

As shown in FIGS. 8A to 8D, in the wild-type mice, VEGF was highly expressed by UVB irradiation, but in the EC-SOD-overexpressed mice, the expression of VEGF was significantly inhibited compared to that in the wild-type mice. These results were consistent with the results of Example 1-2. These results suggest that natural EC-SOD has the effect of inhibiting the expression of angiogenesis-inducing VEGF expression in vivo to inhibit angiogenesis.

<2-4> Examination of Expression Level of MMP-9 in EC-SOD-Overexpressing Mice

The MMP protein degrading an extracellular matrix protein is an important angiogenesis regulatory factor together with VEGF. Particularly, MMP9 is a factor regulating the tumor angiogenesis process through the VEGF-VEGFR system (Bergers et al., Nat. Cell Biol., 2: 737-744, 2000).

Thus, the present inventors examined the expression level of MMP-9 in EC-SOD-overexpressing mice by UVB irradiation.

The back skin tissue of each of the EC-SOD-overexpressing mice, sacrificed in Example 2-1, and the wild-type mice, was mixed with 1 mg/ml gelatin (100 mg/ml) and subjected to SDS-PAGE. Then, the gel was treated with 2.5% Triton X-100 for 20 minutes and washed with water. The gel was incubated with a Zymography reaction solution (1M Tris (pH 7.5), 1M CaCl2, 5M NaCl, 0.2 mM $ZnCl_2$, 25% TX-100, 0.2% $NaN_3$) at 37° C. for 16 hours, stained for 1 hour, decolorized for 1 hour, and then dried in an over for 1 hour. The dried gel was analyzed, and the analysis results are shown in FIG. 9.

Figure 9:
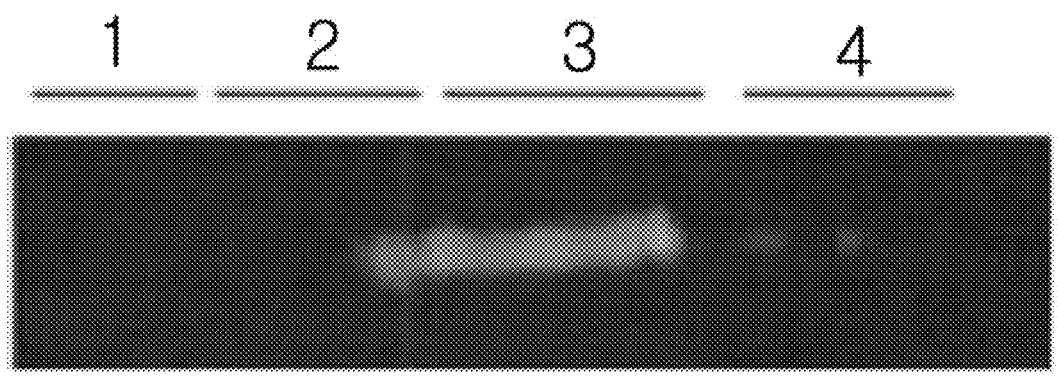
FIG. 9 is a zymography of MMP-9 expression of UV irradiated mouse (Lane 1: wild type mouse, Lane 2: EC-SOD overexpressed mouse, Lane 3: UV irradiated wild type mouse, Lane 4: UV irradiated EC-SOD overexpressed mouse).
Figure 10A:
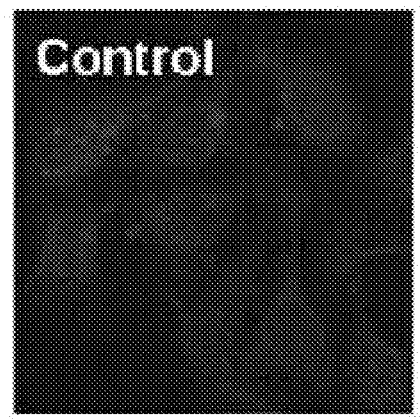
FIGS. 10A-10D are photographs showing VEGF expression in UV irradiated keratinocyte HaCaT cells depending on treating the inventive recombinant EC-SOD using an immunohistological method.
Figure 10B:
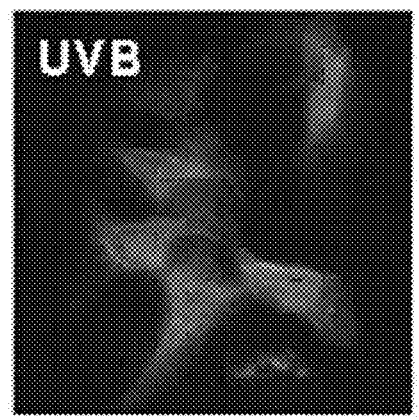
Figure 10C:
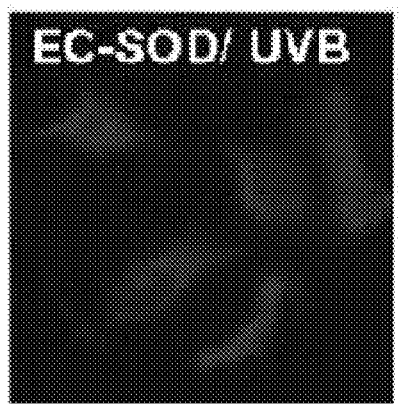
Figure 10D:
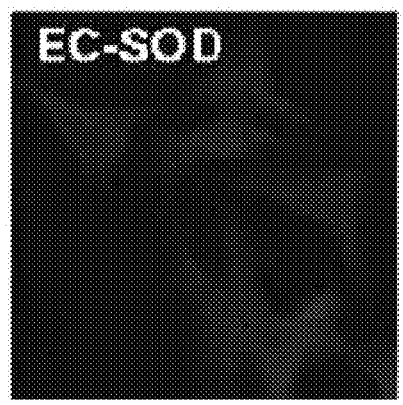

As can be seen in FIG. 9, there was no significant difference in the expression level of MMP-9 between the wild-type mice and the EC-SOD-overexpressed mice before irradiation with UV light. However, due to UVB irradiation, the expression of MMP-9 in the wild-type was increased, but the expression of MMP-9 in the EC-SOD-overexpressed mice was significantly inhibited compared to that in the wild-type mice.

From the above results, it can be seen that the natural EC-SOD protein inhibits the expression of VEGF in vivo, and in addition, inhibits the expression of MMP-9, which is involved in angiogenesis-related signaling through the VEGF-VEGFR system, thus effectively inhibiting angiogenesis.

Example 3

Angiogenesis Inhibitory Effect of Recombinant EC-SOD Protein

Whether the recombinant EC-SOD protein, separated and purified in Example 1, has the effect of inhibiting angiogenesis was examined. Keratinocyte HaCaT cells were plated on 18-mm cover slips at a concentration of $1\times10^4$ cells/cover slip. The cells were cultured in DME medium (Dulbecco's minimum essential medium, GIBCO), containing 10% fetal bovine serum (FBS, GIBCO) and 100 units penicillin and 100 g streptomycin/ml of medium, in 5% $CO_2$ at 37° C. When the adhered cells reached a confluence of 30-40%, the fetal bovine serum was removed, and then cultured for 24 hours. When the cells reached a confluence of 50-60%, the cells were pretreated with 10 μg of EC-SOD. After the cells were treated with the purified recombinant EC-SOD protein for 30 minutes, the cells were treated with UV light at a dose of 100 J, and after 24 hours, the skin keratinocyte cells were fixed with paraformaldehyde and immunostained. The fixed cells were blocked with 10% normal goat serum and washed three times with phosphate buffered saline (PBS). For immunostaining for VEGF (vascular endothelial growth factor), the cells were treated with a rabbit anti-VEGF antibody (Santa Cruz, USA), and then incubated at 4° C. for at least 16 hours. Then, the cells were fluorescence-stained with a FITC-conjugated anti-mouse-IgG secondary antibody (Zymed, USA), and then observed with a fluorescent microscope (Carl Zeiss, Germany).

As a result, as shown in FIGS. 10A to 10D, in the UVB group where the cells were irradiated with UVB, the expression of VEGF in the cells was significantly increased compared to that in the control group not irradiated with UVB. Also, in the EC-SOD/UVB group where the group irradiated with UVB was treated with the recombinant protein, the expression of VEGF was significantly inhibited, suggesting that angiogenesis was inhibited by the recombinant EC-SOD protein.

Example 4

Effect of Recombinant EC-SOD Protein on Proliferation and Differentiation of T Cells <4-1> Examination of Effect of Recombinant EC-SOD on Proliferation of T Cells Whether EC-SOD has an effect on immune T cells, the following test was examined in the following manner using specific antigen (ovalbumin)-reactive TCR (T cell receptor)- transfected mice (DO.11.10 provided by professor Young-Chul Sung, Pohang University of Science and Technology).

In order to examine whether EC-SOD has an effect on the proliferation of T cells, cells isolated from the spleen of the transfected mice were cultured with the antigen ova peptide for 72 hours, and then cultured with $^3$H for 16 hours. Then, the radiation dose of the cultured cells was measured to examine the proliferation.

Figure 11:
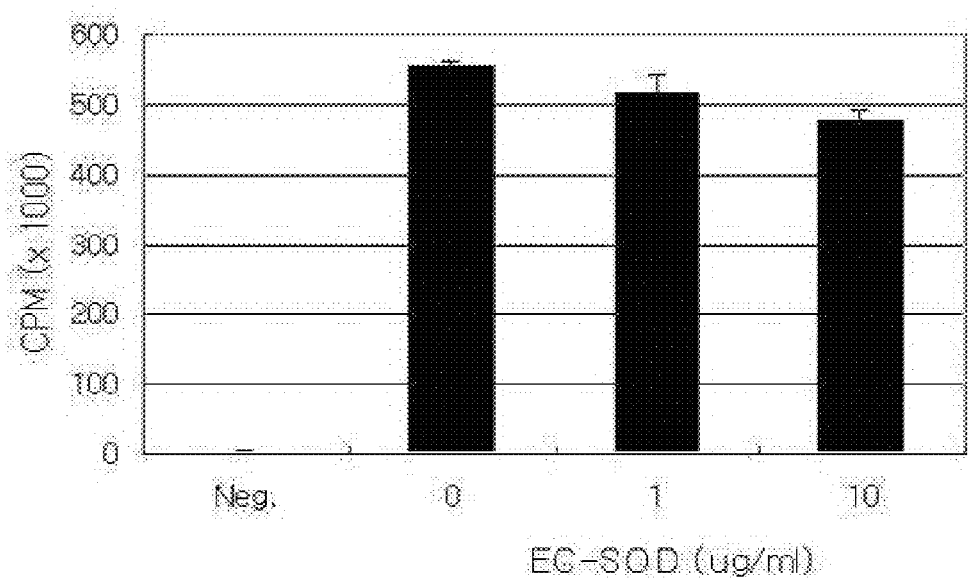
FIG. 11 is a result confirming whether treatment of recombinant EC-SOD protein has the effect on T-cell proliferation (Neg: negative control)

As a result, as can be seen in FIG. 11, there is little or no difference in radiation doses between the group treated without EC-SOD and the groups treated with EC-SOD at concentrations of 1 μg/ml and 10 μg/ml, respectively, suggesting that EC-SOD had little or no effect on the proliferation of T cells.

<4-2> Examination of Effect of Recombinant EC-SOD on Differentiation of T Cells

Although recombinant EC-SOD has no effect on the proliferation of T cells, it can have an effect on the differentiation of T cells. For this reason, T cell cytokines were measured to examine the differentiation of T cells.

Spleen cells were cultured with the antigen ova peptide for 48 hours, and then IL-4 (interleukin-4) produced in the culture medium was measured. The measurement was carried out using an ELISA-kit (Becton, Dickinson and Company, USA) according to the manufacturer's instruction.

Figure 12:
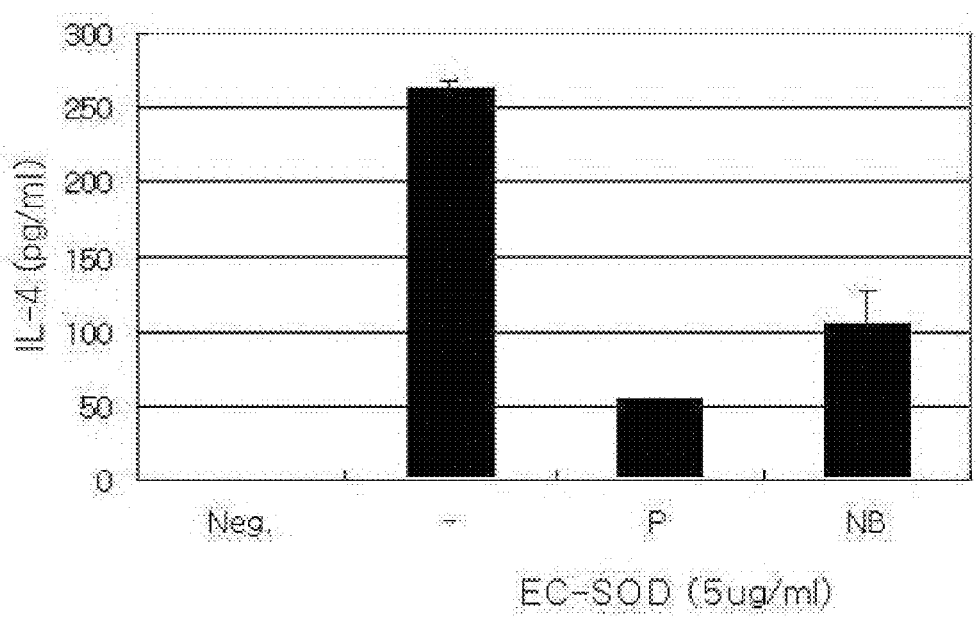
FIG. 12 is a result confirming by identifying the secretion level of IL-4 whether treatment of recombinant EC-SOD protein has the effect on T-cell differentiation (neg.: negative control, –: treated with antigen (Ova peptide) only, p: treated with antigen (Ova peptide) and PBS containing EC-SOD together, NB: treated with antigen (Ova peptide) and Sodium borate containing EC-SOD together).

As a result, as can be seen in FIG. 12, EC-SOD reduced the formation of IL-4. This suggests that EC-SOD has an effect on the differentiation of T cells. In FIG. 12, neg.: a test group not treated with an antigen; –: a test group treated only with an antigen (Ova peptide) p: a test group treated with an antigen (Ova peptide) together with EC-SOD in PBS NB: a test group treated with an antigen (Ova peptide) together with EC-SOD in sodium borate. All the test groups were treated in culture media for 48 hours.

In order to specifically examine the effect of the inventive recombinant EC-SOD on the differentiation of T cells, the recombinant EC-SOD protein was administered into the T-cells of mice, and the amounts of production of cytokines, such as IL-4 and IFN-γ, were compared.

Specifically, from the spleen of DO 11.10 mice provided by Professor Young-Chul Sung, Pohang University of Science and Technology) overexpressing a TCR (T cell receptor) gene recognizing a specific antigen Ova peptide, CD4 T cells were isolated using MACS (Miltenyi Biotech). As antigen-presenting cells, the spleen cells of normal Balb/c mice were subjected to γ-irradiation, and then cultured with the Ova peptide (1 μg/ml, Ova323-339, Peptron) and the CD4 T cells isolated using MACS, in RPMI1640 medium supplemented with 10% FBS. During the culture process, the recombinant EC-SOD protein, separated and purified in Example 1, was added to the culture medium. After 72 hours, the culture medium was collected, and the amounts of IL-4 and IFN-γ in the culture medium were measured using ELISA (antibody: Becton Dickinson).

Figure 13B:
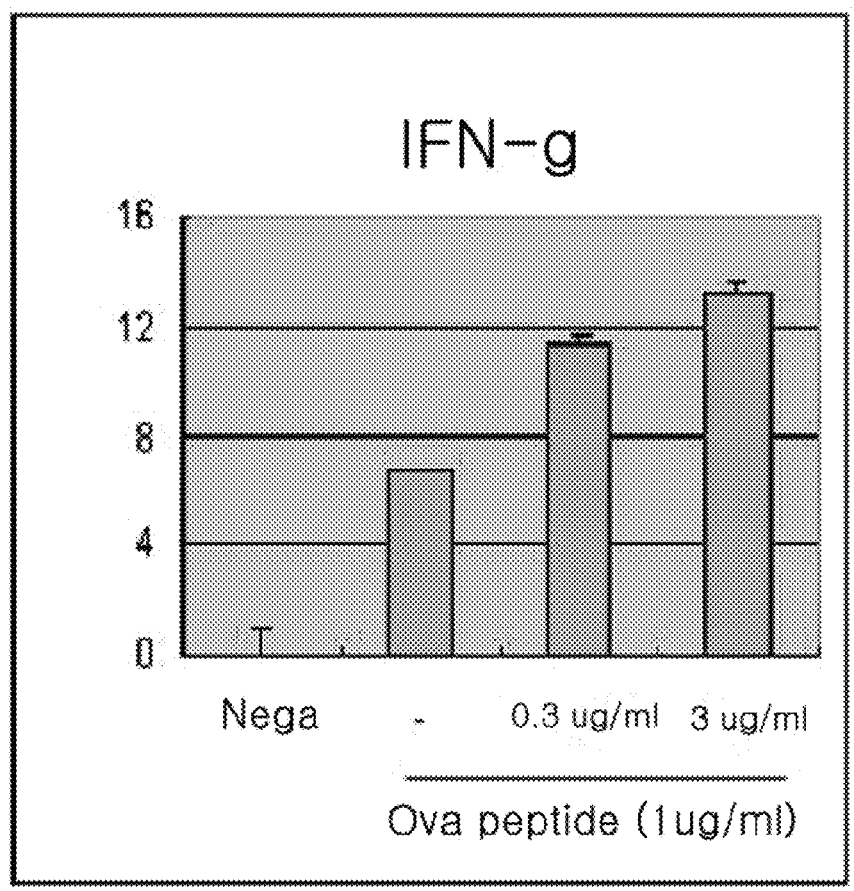
Figure 14A:
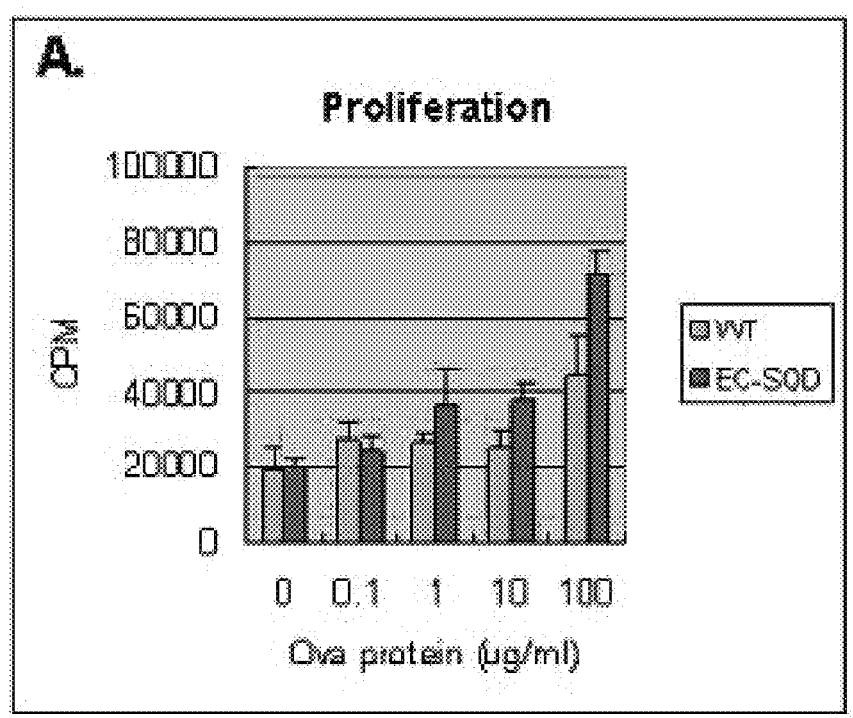
FIGS. 14A and 14B are results showing the effect of EC-SOD on cell proliferation (FIG. 14A) and cytokine generation (FIG. 14B) when an Ova protein and an immune adjuvant CFA (Complete Freund's Adjuvant) was administered into human EC-SOD protein-overexpressed mice.
Figure 14B:
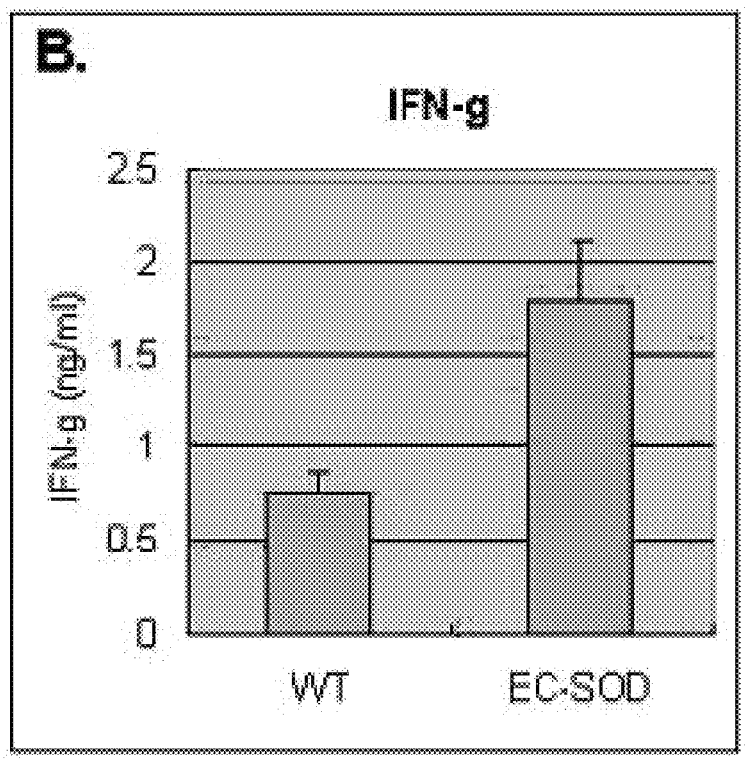
Figure 15A:
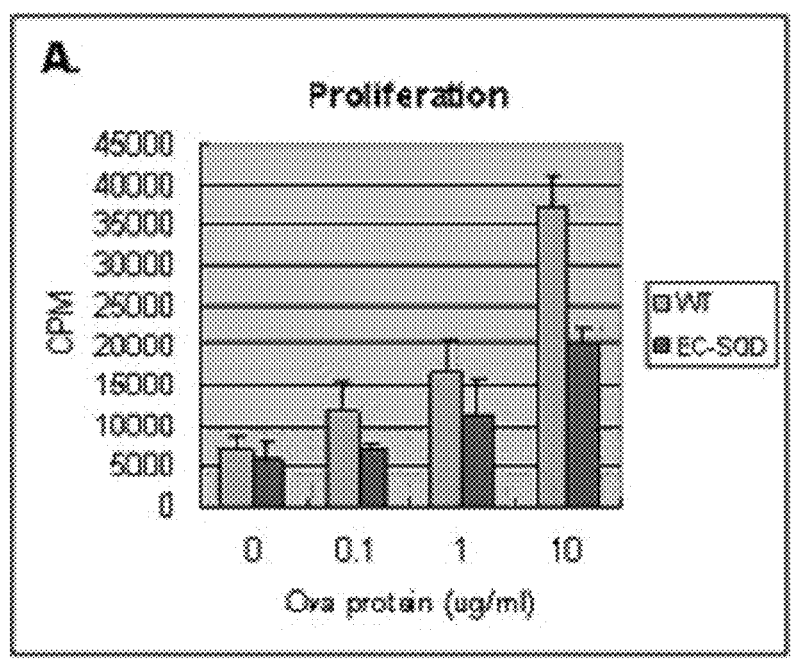
FIGS. 15A and 15B are results showing the effect of EC-SOD on cell proliferation (FIG. 15A) and cytokine generation (FIG. 15B) when an Ova protein and an immune adjuvant Alum (Aluminum Hydroxide) was administered into human EC-SOD protein-overexpressed mice.
Figure 15B:
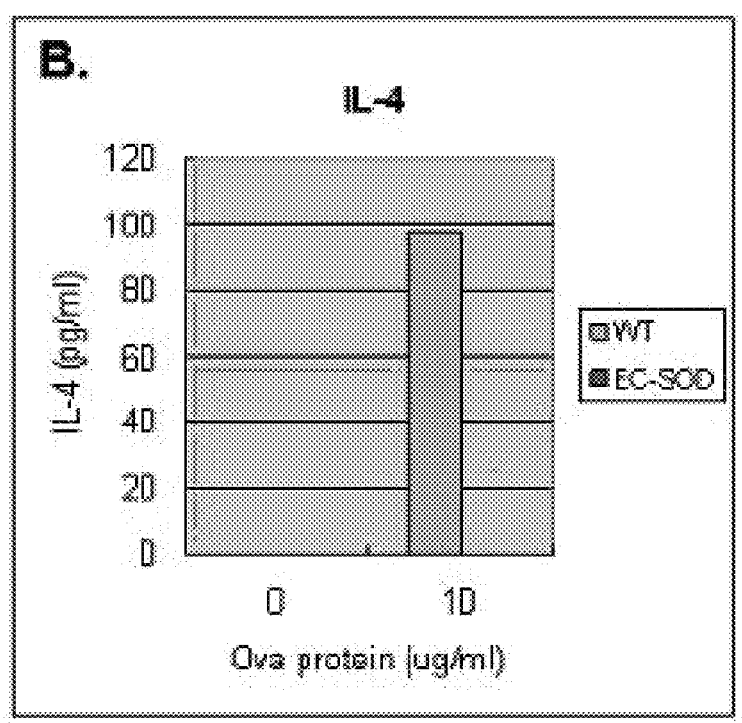

As a result, as can be seen in FIGS. 13A and 13B, the recombinant EC-SOD protein, separated and purified in Example 1, induced the formation of Th1 cytokine IFN-γ in T cells and inhibited the formation of Th2 cytokine IL-4. This suggests that the recombinant EC-SOD protein had an effect on immune cells, particularly on the differentiation of T cells.

Accordingly, it can be seen that the recombinant EC-SOD protein of the present disclosure blocks the over-differentiation of Th2 cells inducing allergic diseases and induces differentiation into Th1 cells, and thus, it can be advantageously used to treat or prevent allergic diseases.

Example 5

Effect of Natural EC-SOD Protein on Differentiation of T Cells

An Ova protein and an immune adjuvant CFA (Complete Freund's Adjuvant, Sigma) inducing Th1 immunity were mixed with alum (aluminum hydroxide, Pierce) inducing Th2 immunity, and 25 μg of the mixture was immunized into the foot sole and tail of the human EC-SOD-overexpressed mice, prepared in Test Example 1. After 11 days, from lymphocytes having inflammation occurred therein, cells were isolated and observed to examine whether EC-SOD had effects on cell proliferation and cytokine production.

In the observation of cell proliferation, $5 \times 10^5$ lymphocytes were cultured in a 96-well plate, and after 3 days of the culture, isotope $^3$H was added to the culture medium. After 16 hours, the proliferation of the cells was observed by measuring the content of the isotope in the cells using a β-counter. Also, in order to examine whether the reaction is an antigen-specific reaction, cell proliferation was observed using varying amounts of the Ova protein. To observe the expression of cytokines, $5 \times 10^6$ lymphocytes were cultured in a 46-well plate, and after 72 hours, the culture medium was collected, and the amounts of IL-4 and IFN-γ in the culture medium were measured using ELISA. The measurement results are shown in FIGS. 14A, 14B, 15A, and 15B.

As shown in FIGS. 14A, 14B, 15A, and 15B, it was observed that, when CFA inducing Th1 differentiation was used as an immune adjuvant, the proliferation of lymphocytes was slightly increased compared to the expression of lymphocytes in the normal mice, and the expression of IFN-γ was increased. It was also observed that, when alum inducing Th2 differentiation was used as an immune adjuvant, the proliferation of lymphocytes was reduced compared to the proliferation of lymphocyte in the normal mice, and the expression of IL-4 was reduced. Such results suggest that EC-SOD has an effect on the differentiation of T cells, that is, it stimulates differentiation into Th1 and inhibits differentiation into Th2.

Accordingly, it can be seen that the natural EC-SOD protein blocks the over-differentiation of Th2 cells inducing allergic diseases and induces differentiation into Th1 cells, and thus it can be advantageously used to treat or prevent allergic diseases.

Example 6

Examination of Effect of Recombinant EC-SOD Protein on Inhibition of Transcriptional Factor Activity In order to examine the effect of EC-SOD on NF-κB activation caused by UV light, HaCaT cells were plated on a 14-mm culture slide, and then cultured in 10% fetal bovine serum-containing DMEM (Dulbecco's modified Eagle's medium) for 24 hours. After 24 hours of the culture, the cells were starved in 1% fetal bovine serum-containing DMEM medium for 24 hours. After the starvation, the cells were pretreated with 10 μg of EC-SOD for 30 minutes, and then washed three times with phosphate buffered saline (PBS). To induce the activation of NF-κB, the cells were then irradiated with UV light at a dose of 100 J/m$^2$. Immediately after the UV light irradiation, the cells were washed again with phosphate buffered saline, treated with 10 μg of EC-SOD, and then further cultured in 1% fetal bovine serum-containing DMEM medium for 4 hours. Then, the cells were fixed with methanol and immunostained. The fixed cells were blocked with 10% normal goat serum and washed three times with phosphate buffered saline (PBS). For immunostaining for EC-SOD and NF-κB, the cells were treated with each of a mouse anti-EC-SOD antibody (Lab Frontier, Korea) and a rabbit anti-NF-κB antibody (Santa Cruz, USA) and incubated at 4° C. for at least 16 hours. Then, the cells were fluorescence-stained with TRITC (tetramethyl rhodamine isothiocyanate)-conjugated anti-rabbit IgG secondary antibody, Serotec, GB) and a FITC-fused anti-mouse IgG secondary antibody (Zymed, USA), and then counterstained with Hoechst (Sigma, USA).

Figure 16:
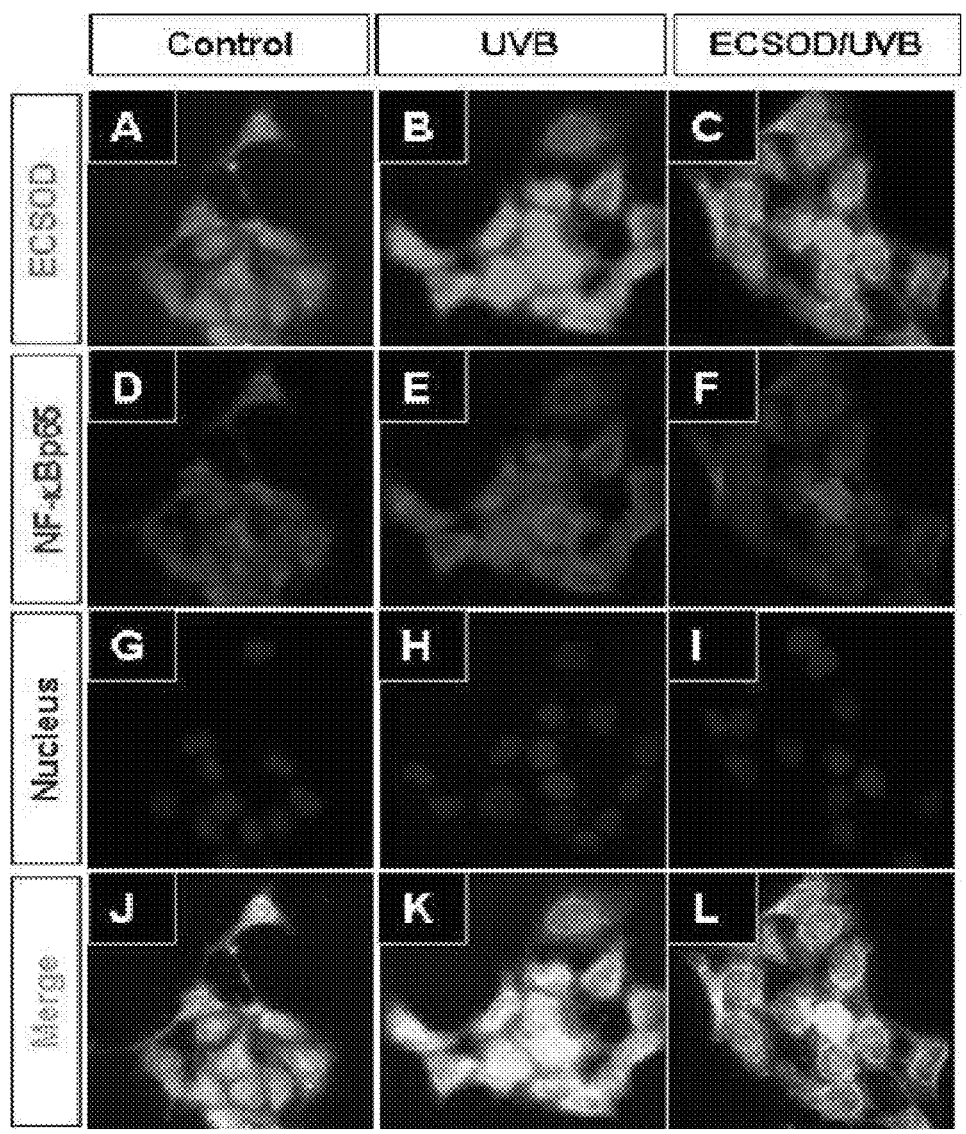
FIG. 16A-L are a result showing the effect of recombinant EC-SOD protein on NF-κB inhibition (Control: EC-SOD transformed HaCaT cell without UVB irradiation, UVB: HaCaT cells with UVB irradiation (100 J/m$^2$), EC-SOD/UVB: HaCaT cells treated with recombinant EC-SOD protein and UVB irradiation (100 J/m$^2$).

As a result, as shown in FIG. 16 (200× magnification), it could be observed that, in the control group where the HaCaT cells transfected with EC-SOD were not irradiated with UV light, NF-κB was not immunostained in the cytoplasm and the nucleus, suggesting that NF-κB was inactivated (FIGS. 16A, D, G and J). It was also observed that, in the UVB group (where the HaCaT cells were irradiated with UVB at a dose of 100 J/$m^2$), NF-κB was rapidly activated at the nuclear site and the perinuclear site (FIGS. 16B, E, H and K). In comparison with this, it was observed that, in the EC-SOD/UVB group (where HaCaT cells were treated with the inventive recombinant EC-SOD protein and irradiated with 100 J/$m^2$ of UVB), the activation of NF-κB at the nuclear site was significantly inhibited compared to that in the UVB group (FIGS. 16C, F, I and L). Such results revealed that the recombinant EC-SOD protein of the present disclosure inhibits the activation of the transcriptional factor NF-κB.

Accordingly, it can be seen that the recombinant EC-SOD protein of the present disclosure inhibits the abnormal activation of NF-κB, and thus it can be used to prevent or treat autoimmune diseases, such as allergies.

Example 7

Examination of Effect of EC-SOD Protein on Reduction of Human Mast Cell Degranulation In order to examine whether EC-SOD has an effect on the degranulation of human mast cells, mast cells were stained with toluidine blue, and then the number of degranulated cells among 100 stained cells was counted.

Human mast cells (semi-adhesion, Human Mast Cell-1 (HMC-1) provided by professor Hyung-Min Kim, Kyunghee University) were plated on 18×18 mm cover slips at a concentration of 1×$10^4$ cells/cover slip. The cells were cultured in IMDM medium (Isocove's modified Dulbecco's medium, GIBCO), containing 10% fetal bovine serum (FBS, GIBCO) and 100 units penicillin and 100 g streptomycin/ml of medium, in 5% $CO^2$ at 37° C. Because the cells were semi-adhesion cells, the ratio of adhered cells to non-adhered cells was about 4:6. When the adhered cells reached a confluence of about 30-40%, the cells were pretreated with 5 μg of EC-SOD for 1 hour, and then treated with 1 μM of calcium channel A23187 and 50 nM of phorbol 12-myristate 13-acetate (PMA) to increase the concentration of calcium in the cells.

After 12 hours, the human mast cells were washed with phosphate buffered saline (PBS), and then fixed with 4% paraformaldehyde for 10 minutes. After the cells were washed with phosphate buffered saline, they were stained with a solution of 0.1% toluidine blue in 1% acidic saline (pH 2.3) for 2-3 minutes. After the cells were washed again with water, the cells were dehydrated with 95% and 100% alcohol and fixed with xylene, and the number of degranulated cells among 100 stained cells was counted.

Figure 17A:
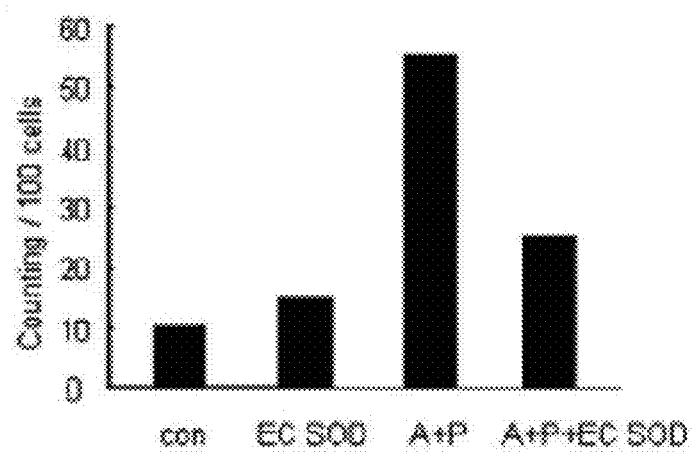
FIGS. 17A and 17B are photographs showing mast cell degranulation inhibition activity of recombinant EC-SOD protein (FIG. 17A) and its microscopic picture (FIG. 17B) (Con: human mast cells group without treatment, EC-SOD: EC-SOD treated group, A+P: group having high cellular concentration of calcium, A+P+EC-SOD: group pretreated with EC-SOD and having high cellular concentration of calcium).
Figure 17B:
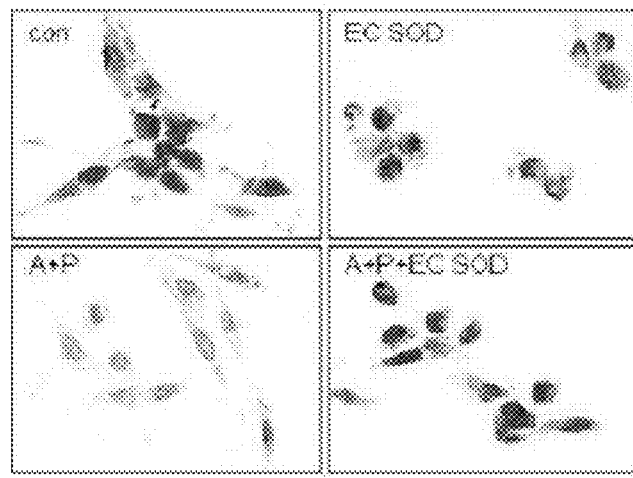

As a result, as shown in FIG. 17A, the number of degranulated cells in the human mast cell group (control) not treated with anything was 10, and the number of degranulated cells in the group (EC-SOD) treated with EC-SOD was 16. In comparison with this, in the group (A+P) where the concentration of calcium in the cells was increased to induce the activation and degranulation of the mast cells, the number of degranulated cells was increased five-fold to 55, but in the group (A+P+EC-SOD) where the cells were pretreated with EC-SOD and treated to increase the concentration of calcium in the cells, the number of degranulated cells was reduced again to 25. This indicates that the reduction of mast cell degranulation occurred due to the inhibition of reactive oxygen species caused by the action of EC-SOD. A micrograph showing the degranulation of the mast is shown in FIG. 17B.

Accordingly, in view of the fact that mediators, such as histamine, stored in mast cells, are released due to the degranulation of the mast cells to cause inflammatory reactions, such as allergies, it can be seen that the recombinant EC-SOD protein of the present disclosure can be advantageously used to prevent or treat allergies.

Example 8

Inhibitory Effect of Natural EC-SOD Protein and Recombinant EC-SOD (209 EC-SOD) Against Corneal Neovascularization and Lymphangiogenesis The 8 week-old male C57BL/6J mice were anesthetized with an intramuscular injection of 20 mg/kg of ketamine and 8 mg/kg of xylazine. One 10-0 nylon sutures (Ethicon, NJ, USA) was placed intrastromally. The outer point of suture placement was chosen near the limbus corneae, and the inner suture point was chosen near the corneal center equidistant from the limbus corneae. Infiltration of blood vessels and lymphatic vessels were generated by SICNV model in mice (n=5/group). After two weeks, corneal angiogenesis and lymphangiogenesis were determined by staining with CD31 and LYVE-1, and blood vessels (BV) density, lymphatic vessels (LV) density were measured (Scale bars=500 μm). Natural EC-SOD or recombinant EC-SOD (209 EC-SOD) (100 U in 10 ul) was injected into subconjunctiva.

Figure 18A:
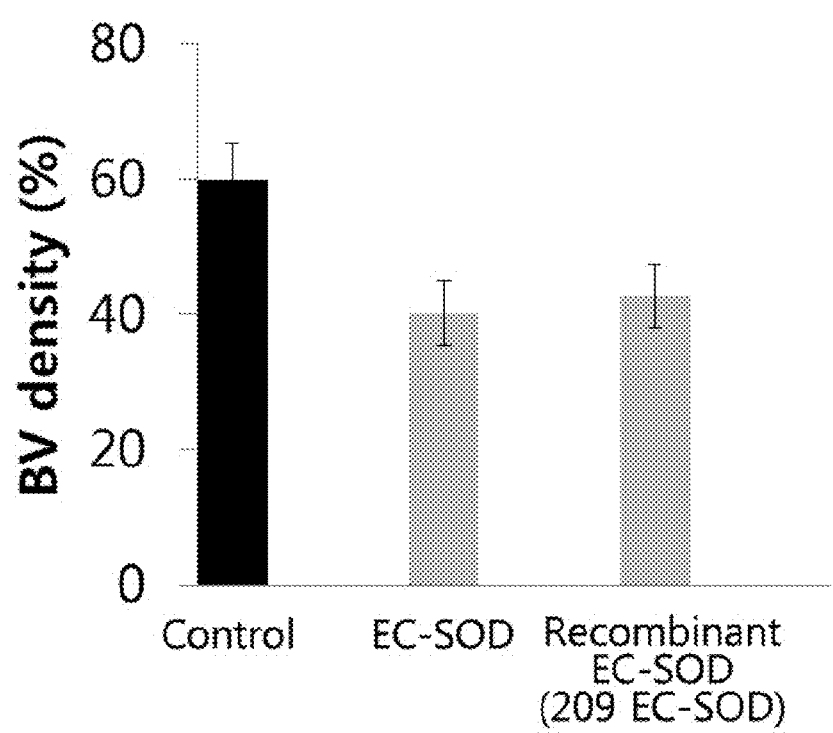
FIGS. 18A and 18B illustrate diagrams showing the mean values for blood vessels (BV) density (FIG. 18A) and lymphatic vessels (LV) density (FIG. 18B) in corneal neovascularization C57BL/6J mice model.

The mean value for blood vessels (BV) density observed for each test group is as follows: 59.8±5.43 for the control group, whereas 40.1±4.86 (p<0.05 vs. control) for natural EC-SOD-treated group and 42.8±4.71 (p<0.05 vs. control) for recombinant EC-SOD (209 EC-SOD)-treated group, respectively (See FIG. 18A).

Figure 18B:
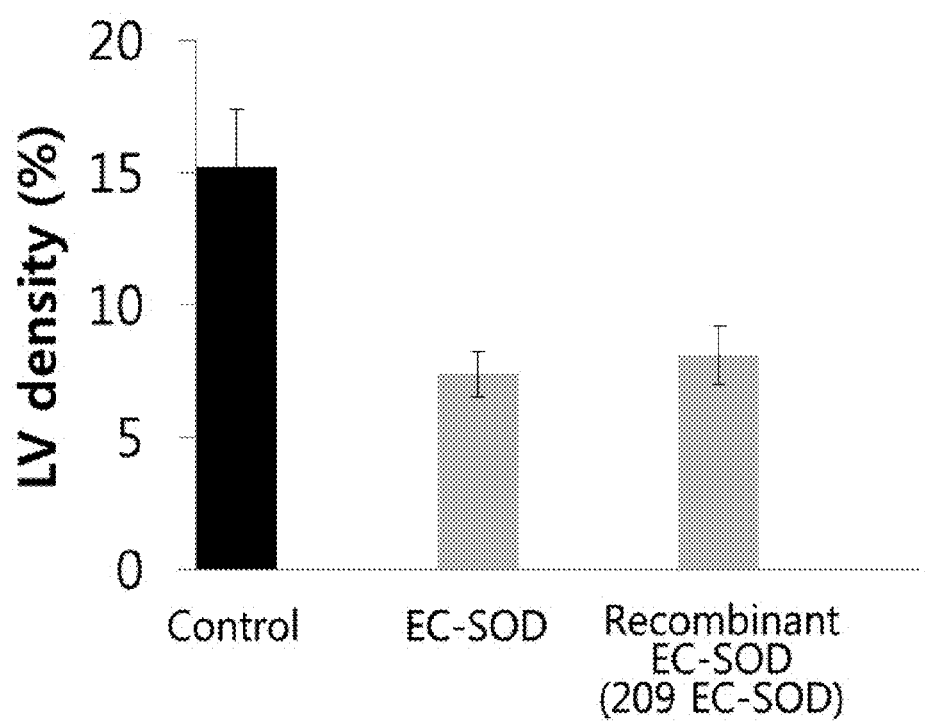

Further, the mean value for lymphatic vessels (LV) density observed for each test group is as follows: 15.2±2.18 for the control group, whereas 7.4±0.86 (p<0.05 vs. control) for natural EC-SOD-treated group and 8.1±1.1 (p<0.05 vs. control) for recombinant EC-SOD (209 EC-SOD)-treated group, respectively (See FIG. 18B).

Example 9

Inhibitory Effect of Natural EC-SOD Protein and Recombinant EC-SOD (209 EC-SOD) Against Retinal Angiogenesis The Oxygen-Induced Retinopathy (OIR) model using C57BL/6J mice pups was utilized for the purpose of observing the anti-angiogenic effect of EC-SOD protein. The newborn C57BL/6J mice at P7 stage of development and their nursing mothers were exposed to 75% of oxygen in a hyperoxic chamber (ProOx Model 110, BioSpherix, NY, USA) for 5 days, and then were returned to room air for 5 days. The retinas of OIR mice developed extensive vascular regression in the central region and pathologic neovascular tufts (NVT) in the middle and peripheral regions. 100 U of full length EC-SOD or recombinant EC-SOD (209 EC-SOD) protein was intraperitoneally injected twice a day from postnatal 12 days. The anti-angiogenic effect was observed at postnatal 17 days.

Figure 19A:
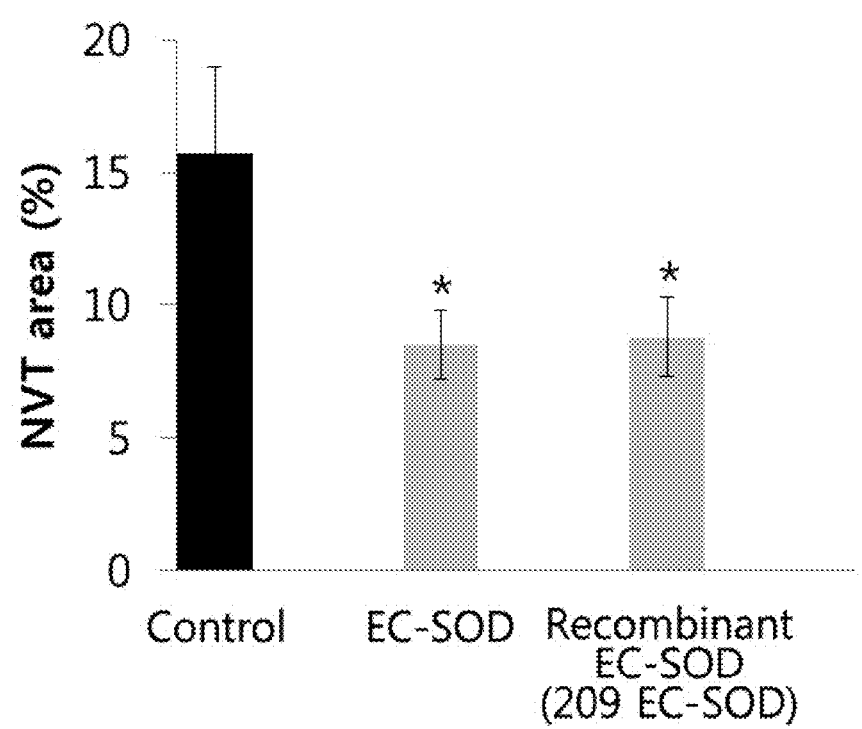
FIGS. 19A-19C illustrate diagrams showing the area of retinal angiogenesis (%) (FIG. 19A), the area of avascular regions (%) (FIG. 19B), and the area of leakage and hemorrhage region (TER119 stain) (%) (FIG. 19C) in Oxygen-induced retinopathy (OIR) C57BL/6J mice model.

FIG. 19A shows that the area of retinal angiogenesis (%) was observed as 15.7±3.28 for the control group, whereas 8.5±1.29 (p<0.01 vs. control) for natural EC-SOD-treated group, and 8.8±1.48 (p<0.01 vs. control) for recombinant EC-SOD (209 EC-SOD)-treated group, respectively.

Figure 19B:
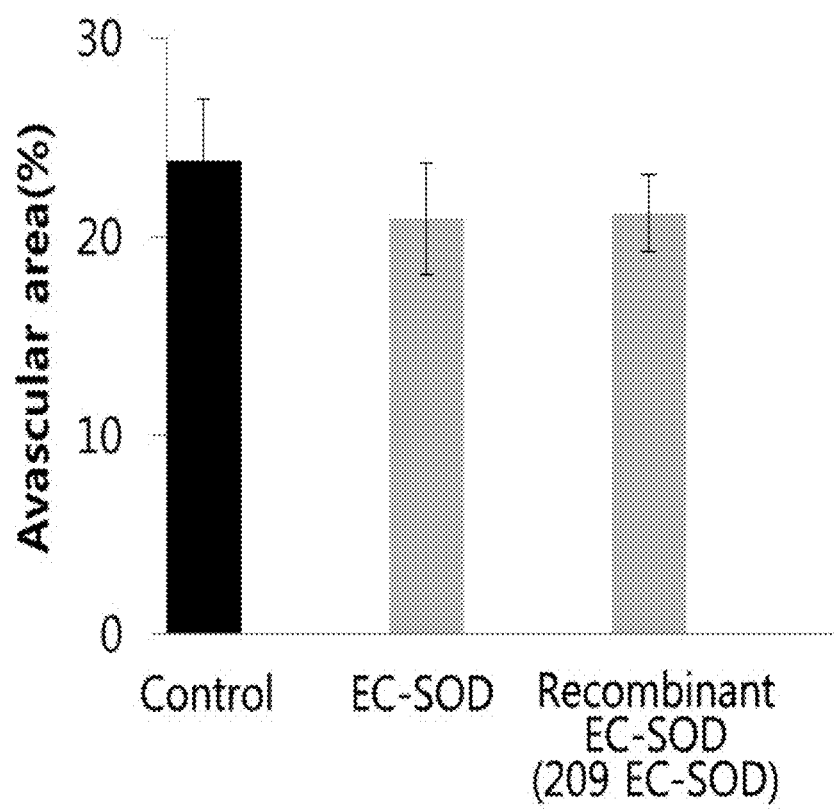

Further, FIG. 19B shows that the area of avascular regions (%) was observed as 23.8±3.16 for the control group, whereas 20.9±2.81 (p<0.01 vs. control) for natural EC-SOD-treated group and 21.2±1.92 (p<0.01 vs. control) for recombinant EC-SOD (209 EC-SOD)-treated group, respectively.

Figure 19C:
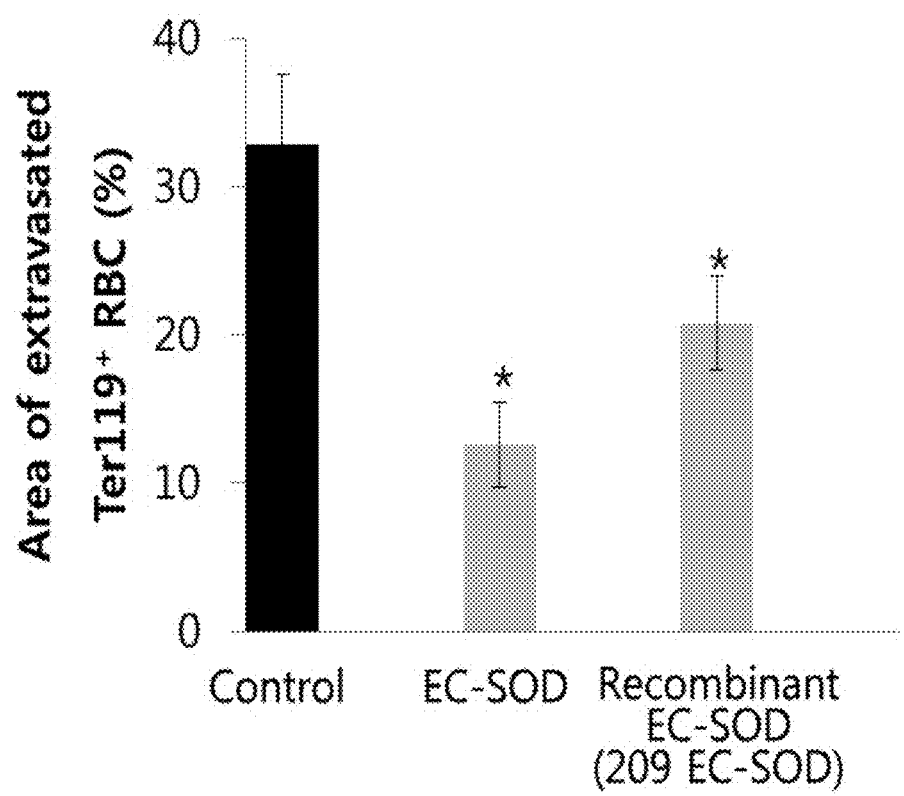

FIG. 19C shows that the area of leakage and hemorrhage region (TER119 stain) (%) was observed as 32.8±4.81 for the control group, whereas 12.6±2.89 (p<0.01 vs. control) for natural EC-SOD-treated group and 20.8±3.12 (p<0.01 vs. control) for recombinant EC-SOD (209 EC-SOD)-treated group, respectively.

Example 10

Inhibitory Effect of Natural EC-SOD Protein and Recombinant EC-SOD (209 EC-SOD) Against Choroidal Neovascularization The laser-induced choroidal neovascularization model using SD rat was confirmed for the purpose of observing the anti-angiogenic effect of natural EC-SOD and recombinant EC-SOD (209 EC-SOD) protein. The choroidal neovascularization (CNV) was induced under general anesthesia with an intramuscular injection of ketamine (20 mg/kg) and xylasine (8 mg/kg), supplemented with topical anesthesia (paraprocaine hydrochloride, 0.4%). Pupils were dilated with topical 1% tropicamide (Santen, Osaka, Japan). A warming pad maintained the body temperature of the rat during the procedure. Four burns were made by 532 nm argon laser photocoagulation (0.1 mm spot size; 0.05 s duration; 200 mW) in each retina, via a slit lamp delivery system (Coherent, Novus 2000, USA) with a 5.4 mm hand-held contact fundus lens (Ocular Instruments, Bellevue, Wash.). Burns were placed at the 3 o'clock positions around the optic disc. Production of a bubble (indicating rupture of Bruch's membrane) without bleeding at the time of laser hitting was considered a valid burn. Lesions in which the four laser spots became confluent were also excluded from the later observation. Careful examination was performed after injection using a slit lamp. It was found that no animals had traumatic cataract or vitreous hemorrhage. 100 U (10 ul) of natural EC-SOD and recombinant EC-SOD (209 EC-SOD) protein was injected into the vitreous body after laser injury, immediately. To measure vascular leakage 2 week later, 2% fluorescein was intravenously injected 30 seconds prior to fluorescein angiography.

Figure 20:
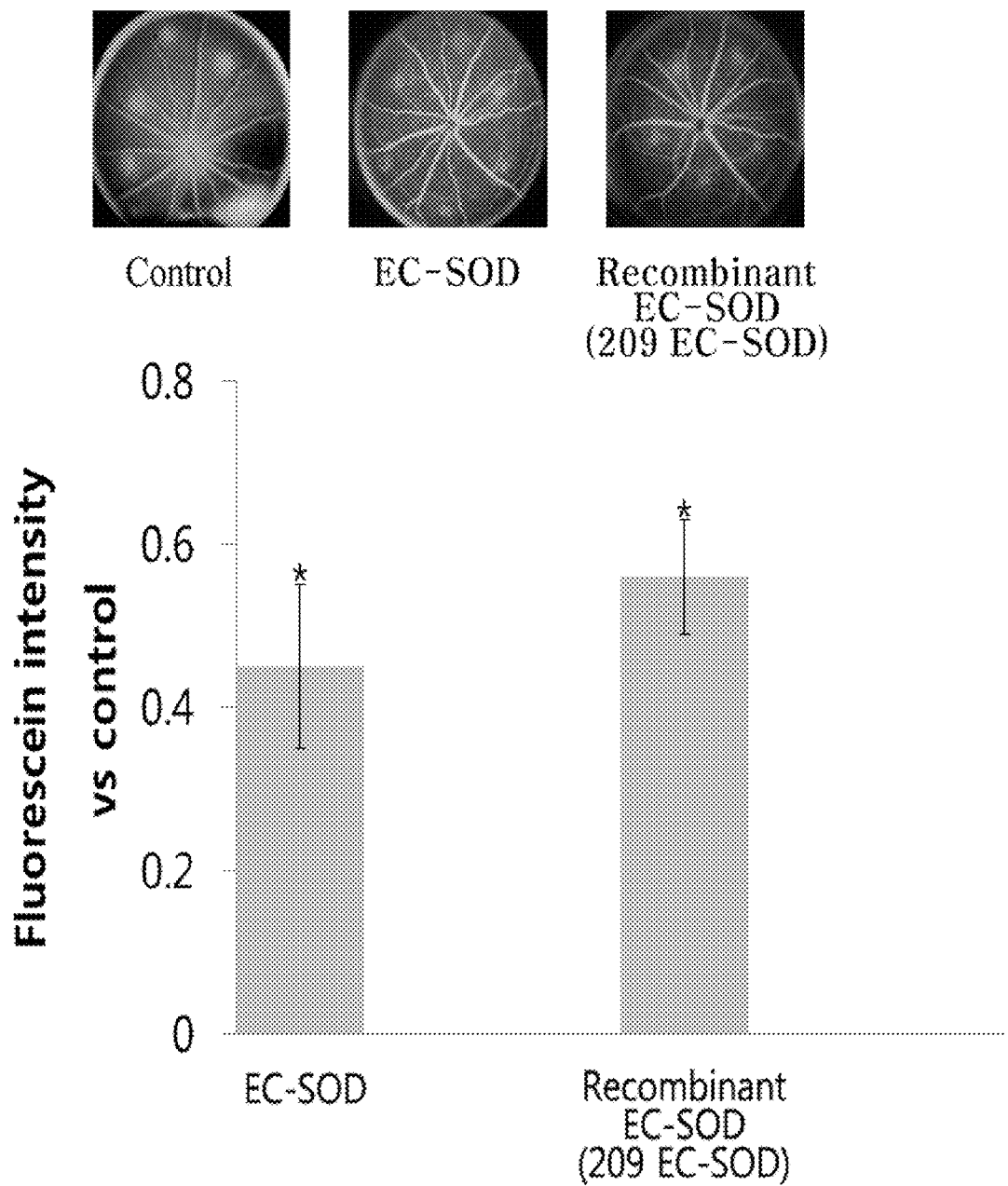
FIG. 20 shows the observation of fluorescein angiography and intensity in choroidal neovascularization rat CNV model.

The vascular leakage was observed by fluorescein intensity in injury region. As shown in FIG. 20, the fluorescein intensity (ratio vs. control) was observed as 0.45±0.1 (p<0.01 vs. control) for natural EC-SOD-treated group and 0.56±0.07 (p<0.01 vs. control) for recombinant EC-SOD (209 EC-SOD)-treated group, respectively, demonstrating that both natural EC-SOD protein and recombinant EC-SOD (209 EC-SOD) significantly inhibited retinal angiogenesis in CNV model.

What is claimed is:

1. A method for treating an angiogenesis-mediated eye disease, comprising a subject in need thereof receiving an effective amount of an EC-SOD protein,
   the EC-SOD protein consisting of an amino acid sequence SEQ ID NO: 1 or 3,
   wherein the angiogenesis-mediated eye disease is selected from the group consisting of diabetic retinopathy, retinopathy of prematurity, neovascular glaucoma, corneal diseases caused by angiogenesis, degenerative spots, macular degeneration, pterygium, retinal degeneration, retrolental fibroplasia, wet type macular degeneration, choroidal neovascularization and corneal graft rejection.

* * * * *

SEQUENCE LISTING

```
<160> NUMBER OF SEQ ID NOS: 10

<210> SEQ ID NO 1
<211> LENGTH: 209
<212> TYPE: PRT
<213> ORGANISM: Artificial Sequence
<220> FEATURE:
<223> OTHER INFORMATION: recombinant EC-SOD

<400> SEQUENCE: 1

Trp Thr Gly Glu Asp Ser Ala Glu Pro Asn Ser Asp Ser Ala Glu Trp
 1               5                  10                  15

Ile Arg Asp Met Tyr Ala Lys Val Thr Glu Ile Trp Gln Glu Val Met
                20                  25                  30

Gln Arg Arg Asp Asp Asp Gly Thr Leu His Ala Ala Cys Gln Val Gln
            35                  40                  45

Pro Ser Ala Thr Leu Asp Ala Ala Gln Pro Arg Val Thr Gly Val Val
        50                  55                  60

Leu Phe Arg Gln Leu Ala Pro Arg Ala Lys Leu Asp Ala Phe Phe Ala
    65                  70                  75                  80

Leu Glu Gly Phe Pro Thr Glu Pro Asn Ser Ser Ser Arg Ala Ile His
                85                  90                  95

Val His Gln Phe Gly Asp Leu Ser Gln Gly Cys Glu Ser Thr Gly Pro
            100                 105                 110

His Tyr Asn Pro Leu Ala Val Pro His Pro Gln His Pro Gly Asp Phe
        115                 120                 125

Gly Asn Phe Ala Val Arg Asp Gly Ser Leu Trp Arg Tyr Arg Ala Gly
```

```
                130                   135                   140
Leu Ala Ala Ser Leu Ala Gly Pro His Ser Ile Val Gly Arg Ala Val
145                 150                 155                 160

Val Val His Ala Gly Glu Asp Asp Leu Gly Arg Gly Gly Asn Gln Ala
                165                 170                 175

Ser Val Glu Asn Gly Asn Ala Gly Arg Arg Leu Ala Cys Cys Val Val
                180                 185                 190

Gly Val Cys Gly Pro Gly Leu Trp Glu Arg Gln Ala Arg Glu His Ser
            195                 200                 205

Glu

<210> SEQ ID NO 2
<211> LENGTH: 627
<212> TYPE: DNA
<213> ORGANISM: Artificial Sequence
<220> FEATURE:
<223> OTHER INFORMATION: recombinant EC-SOD

<400> SEQUENCE: 2
tggacgggcg aggactcggc ggagcccaac tctgactcgg cggagtggat ccgagacatg    60
tacgccaagg tcacggagat ctggcaggag gtcatgcagc ggcgggacga cgacggcacg   120
ctccacgccg cctgccaggt gcagccgtcg gccacgctgg acgccgcgca gccccgggtg   180
accggcgtcg tcctcttccg gcagcttgcg ccccgcgcca agctcgacgc cttcttcgcc   240
ctggagggct ccccgaccga gccgaacagc tccagccgcg ccatccacgt gcaccagttc   300
ggggacctga gcagggctg cgagtccacc gggccccact acaacccgct ggccgtgccg   360
cacccgcagc acccgggcga cttcggcaac ttcgcggtcc gcgacggcag cctctggagg   420
taccgcgccg gctggccgc ctcgctcgcg ggcccgcact ccatcgtggg ccgggccgtg   480
gtcgtccacg ctggcgagga cgacctgggc cgcggcggca accaggccag cgtggagaac   540
gggaacgcgg gccggcggct ggcctgctgc gtggtgggcg tgtgcgggcc cgggctctgg   600
gagcgccagg cgcgggagca ctcagag                                       627

<210> SEQ ID NO 3
<211> LENGTH: 240
<212> TYPE: PRT
<213> ORGANISM: homosapiens
<220> FEATURE:
<223> OTHER INFORMATION: Human EC-SOD

<400> SEQUENCE: 3

Met Leu Ala Leu Leu Cys Ser Cys Leu Leu Leu Ala Ala Gly Ala Ser
1               5                   10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
        35                  40                  45

Val Met Gln Arg Arg Asp Asp Asp Gly Thr Leu His Ala Ala Cys Gln
    50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
                85                  90                  95

Phe Ala Leu Glu Gly Phe Pro Thr Glu Pro Asn Ser Ser Ser Arg Ala
            100                 105                 110
```

```
Ile His Val His Gln Phe Gly Asp Leu Ser Gln Gly Cys Glu Ser Thr
        115                 120                 125
Gly Pro His Tyr Asn Pro Leu Ala Val Pro His Pro Gln His Pro Gly
130                 135                 140
Asp Phe Gly Asn Phe Ala Val Arg Asp Gly Ser Leu Trp Arg Tyr Arg
145                 150                 155                 160
Ala Gly Leu Ala Ala Ser Leu Ala Gly Pro His Ser Ile Val Gly Arg
                165                 170                 175
Ala Val Val Val His Ala Gly Glu Asp Asp Leu Gly Arg Gly Gly Asn
                180                 185                 190
Gln Ala Ser Val Glu Asn Gly Asn Ala Gly Arg Arg Leu Ala Cys Cys
            195                 200                 205
Val Val Gly Val Cys Gly Pro Gly Leu Trp Glu Arg Gln Ala Arg Glu
        210                 215                 220
His Ser Glu Arg Lys Lys Arg Arg Arg Glu Ser Glu Cys Lys Ala Ala
225                 230                 235                 240

<210> SEQ ID NO 4
<211> LENGTH: 720
<212> TYPE: DNA
<213> ORGANISM: homosapiens
<220> FEATURE:
<223> OTHER INFORMATION: Human EC-SOD

<400> SEQUENCE: 4
atgctggcgc tactgtgttc ctgcctgctc ctggcagccg gtgcctcgga cgcctggacg     60
ggcgaggact cggcggagcc caactctgac tcggcggagt ggatccgaga catgtacgcc    120
aaggtcacgg agatctggca ggaggtcatg cagcggcggg acgacgacgg cacgctccac    180
gccgcctgcc aggtgcagcc gtcggccacg ctggacgccg cgcagccccg ggtgaccggc    240
gtcgtcctct tccggcagct tgcgccccgc gccaagctcg acgccttctt cgccctggag    300
ggcttcccga ccgagccgaa cagctccagc gcgccatcc acgtgcacca gttcggggac    360
ctgagccagg gctgcgagtc caccgggccc cactacaacc cgctggccgt gccgcacccg    420
cagcacccgg gcgacttcgg caacttcgcg gtccgcgacg gcagcctctg gaggtaccgc    480
gccggcctgg ccgcctcgct cgcgggcccg cactccatcg tgggccgggc cgtggtcgtc    540
cacgctggcg aggacgacct gggccgcggc ggcaaccagg ccagcgtgga gaacgggaac    600
gcgggccggc ggctggcctg ctgcgtggtg ggcgtgtgcg ggcccgggct ctgggagcgc    660
caggcgcggg agcactcaga gcgcaagaag cggcggcgcg agagcgagtg caaggccgcc    720

<210> SEQ ID NO 5
<211> LENGTH: 251
<212> TYPE: PRT
<213> ORGANISM: Musculus
<220> FEATURE:
<223> OTHER INFORMATION: Mouse EC-SOD

<400> SEQUENCE: 5

Met Leu Ala Phe Leu Phe Tyr Gly Leu Leu Leu Ala Ala Cys Gly Ser
1               5                   10                  15
Val Thr Met Ser Asn Pro Gly Glu Ser Ser Phe Asp Leu Ala Asp Arg
            20                  25                  30
Leu Asp Pro Val Glu Lys Ile Asp Arg Leu Asp Leu Val Glu Lys Ile
        35                  40                  45
Gly Asp Thr His Ala Lys Val Leu Glu Ile Trp Met Glu Leu Gly Arg
    50                  55                  60
```

```
Arg Arg Glu Val Asp Ala Ala Glu Met His Ala Ile Cys Arg Val Gln
 65                  70                  75                  80

Pro Ser Ala Thr Leu Pro Asp Gln Pro Gln Ile Thr Gly Leu Val
             85                  90                  95

Leu Phe Arg Gln Leu Gly Pro Gly Ser Arg Leu Glu Ala Tyr Phe Ser
            100                 105                 110

Leu Glu Gly Phe Pro Ala Glu Gln Asn Ala Ser Asn Arg Ala Ile His
            115                 120                 125

Val His Glu Phe Gly Asp Leu Ser Gln Gly Cys Asp Ser Thr Gly Pro
130                 135                 140

His Tyr Asn Pro Met Glu Val Pro His Pro Gln His Pro Gly Asp Phe
145                 150                 155                 160

Gly Asn Phe Val Val Arg Asn Gly Gln Leu Trp Arg His Arg Val Gly
                165                 170                 175

Leu Thr Ala Ser Leu Ala Gly Pro His Ala Ile Leu Gly Arg Ser Val
            180                 185                 190

Val Val His Ala Gly Glu Asp Asp Leu Gly Lys Gly Gly Asn Gln Ala
            195                 200                 205

Ser Leu Gln Asn Gly Asn Ala Gly Arg Arg Leu Ala Cys Cys Val Val
210                 215                 220

Gly Thr Ser Ser Ser Ala Ala Trp Glu Ser Gln Thr Lys Glu Arg Lys
225                 230                 235                 240

Lys Arg Arg Arg Glu Ser Glu Cys Lys Thr Thr
                245                 250
```

```
<210> SEQ ID NO 6
<211> LENGTH: 756
<212> TYPE: DNA
<213> ORGANISM: Musculus
<220> FEATURE:
<223> OTHER INFORMATION: Mouse EC-SOD

<400> SEQUENCE: 6
atgttggcct tcttgttcta cggcttgcta ctggcggcct gtggctctgt caccatgtca    60
gatccagggg agtccagctt cgacctagca gacaggcttg acccggttga aagatagac   120
aggcttgacc tggttgagaa gataggcgac acgcatgcca agtgctgga gatctggatg   180
gagctaggac gacgaaggga ggtggatgct gccgagatgc atgcaatctg cagggtacaa   240
ccatcagcca cgctgccacc ggatcagccg cagatcaccg gcttggttct cttccggcag   300
ctggggccgg gctccaggct tgaggcctat ttcagtctgg agggcttccc agctgagcag   360
aacgcctcca accgtgccat ccacgtgcat gagttcgggg acctgagcca gggctgcgat   420
tccaccggcc cgcactacaa cccgatggag gtgccgcacc ctcagcaccc gggcgacttt   480
ggcaacttcg tggtgcgcaa tggccagctc tggaggcatc gcgtcggcct gaccgcgtcg   540
ctggccggac gcactccat cttgggccgc tctgtggtgg tccacgccgg cgaggacgac   600
ctgggtaaag gtggcaacca ggccagcctg cagaacggca tgcaggtcg ccggctcgcc   660
tgctgcgtgg taggcaccag cagctccgcc gcctgggaga gtcagacaaa ggagcgcaag   720
aagcggcggc gggagagcga gtgcaagacc acttaa                            756
```

```
<210> SEQ ID NO 7
<211> LENGTH: 19
<212> TYPE: DNA
<213> ORGANISM: Artificial Sequence
<220> FEATURE:
```

```
<223> OTHER INFORMATION: sense primer

<400> SEQUENCE: 7
ttgtctctaa tagagggtc                                              19

<210> SEQ ID NO 8
<211> LENGTH: 19
<212> TYPE: DNA
<213> ORGANISM: Artificial Sequence
<220> FEATURE:
<223> OTHER INFORMATION: antisense primer

<400> SEQUENCE: 8
tcaagcctgt ctatcttct                                              19

<210> SEQ ID NO 9
<211> LENGTH: 21
<212> TYPE: DNA
<213> ORGANISM: Artificial Sequence
<220> FEATURE:
<223> OTHER INFORMATION: sense primer

<400> SEQUENCE: 9
tagattctgg acgggcgagg a                                           21

<210> SEQ ID NO 10
<211> LENGTH: 22
<212> TYPE: DNA
<213> ORGANISM: Artificial Sequence
<220> FEATURE:
<223> OTHER INFORMATION: antisense primer

<400> SEQUENCE: 10
tactcgagtc actctgagtg ct                                          22
```